United States Patent
Sutton et al.

(10) Patent No.: US 9,642,999 B2
(45) Date of Patent: May 9, 2017

(54) BRACHYTHERAPY APPLICATOR

(75) Inventors: Douglas S. Sutton, Pacifica, CA (US); George D. Hermann, Portola Valley, CA (US); Michael Drews, Palo Alto, CA (US); Gail S. Lebovic, Frisco, TX (US)

(73) Assignee: Varian Medical Systems, Inc., Palo Alto, CA (US)

( * ) Notice: Subject to any disclaimer, the term of this patent is extended or adjusted under 35 U.S.C. 154(b) by 204 days.

(21) Appl. No.: 13/026,041

(22) Filed: Feb. 11, 2011

(65) Prior Publication Data

US 2011/0257459 A1 Oct. 20, 2011

Related U.S. Application Data

(60) Provisional application No. 61/304,269, filed on Feb. 12, 2010.

(51) Int. Cl.
*A61N 5/00* (2006.01)
*A61M 37/00* (2006.01)
*A61N 5/10* (2006.01)
*A61B 17/42* (2006.01)

(52) U.S. Cl.
CPC ....... *A61M 37/0069* (2013.01); *A61N 5/1016* (2013.01); *A61B 17/42* (2013.01); *A61N 2005/1018* (2013.01)

(58) Field of Classification Search
CPC .. A61N 5/1016; A61N 5/1014; A61N 5/1007; A61N 5/1001; A61N 2005/1018; A61M 31/00; A61M 37/0069; A61B 1/32; A61B 17/42

USPC ........................................................ 600/1-8
See application file for complete search history.

(56) References Cited

U.S. PATENT DOCUMENTS

| | | | |
|---|---|---|---|
| 4,350,151 A * | 9/1982 | Scott | 600/225 |
| 5,653,683 A | 8/1997 | D'Andrea | |
| 5,720,717 A | 2/1998 | D'Andrea | |
| 5,863,284 A * | 1/1999 | Klein | 600/3 |

(Continued)

FOREIGN PATENT DOCUMENTS

| | | |
|---|---|---|
| EP | 1681077 | 7/2006 |
| WO | 9962598 | 12/1999 |

(Continued)

OTHER PUBLICATIONS

Amant, F., Moerman, P., Neven, P., Timmerman, D., Van Limbergen, E., and Vergote, I. "Endometrial Cancer," 2005, Lancet, 366: 491-505.*

(Continued)

*Primary Examiner* — Navin Natnithithadha
*Assistant Examiner* — Sunita Reddy
(74) *Attorney, Agent, or Firm* — Houst Consulting

(57) ABSTRACT

Described here are brachytherapy applicators that comprise a modular support matrix. The modular support matrix may define the arrangement of radiation source lumens within the brachytherapy applicator. The modular support matrix can be adjusted to position the radiation sources to obtain a certain dose and dose profile. A series of modular support matrices may be operably connected according to patient anatomy or dosing requirements. Systems and methods for using such modular brachytherapy applicators are also described.

63 Claims, 13 Drawing Sheets

(56) References Cited

U.S. PATENT DOCUMENTS

| | | | |
|---|---|---|---|
| 6,013,019 A * | 1/2000 | Fischell et al. | 600/3 |
| 6,050,930 A | 4/2000 | Teirstein | |
| 6,068,608 A | 5/2000 | Davis | |
| 6,361,487 B1 * | 3/2002 | Green et al. | 600/7 |
| 6,413,204 B1 | 7/2002 | Winkler | |
| 6,875,165 B2 * | 4/2005 | Dejuan et al. | 600/3 |
| 6,923,754 B2 | 8/2005 | Lubock | |
| 7,338,430 B2 | 3/2008 | Lim | |
| 7,357,770 B1 | 4/2008 | Cutrer | |
| 7,497,819 B2 | 3/2009 | White et al. | |
| 7,497,820 B2 | 3/2009 | White et al. | |
| 7,662,082 B2 | 2/2010 | White et al. | |
| 2003/0216768 A1 * | 11/2003 | Gitis et al. | 606/190 |
| 2004/0006305 A1 | 1/2004 | Hebert | |
| 2005/0080313 A1 | 4/2005 | Stewart | |
| 2006/0100475 A1 * | 5/2006 | White et al. | 600/3 |
| 2006/0173232 A1 * | 8/2006 | Lovoi et al. | 600/1 |
| 2007/0173680 A1 | 7/2007 | Rioux | |
| 2007/0219446 A1 | 9/2007 | Beyhan | |
| 2008/0167514 A1 * | 7/2008 | Lim et al. | 600/6 |
| 2008/0214887 A1 | 9/2008 | Heanue | |
| 2008/0221384 A1 * | 9/2008 | Chi Sing et al. | 600/7 |
| 2008/0293994 A1 | 11/2008 | Francescatti | |
| 2008/0300445 A1 * | 12/2008 | Francescatti et al. | 600/6 |
| 2008/0305075 A1 * | 12/2008 | Curd et al. | 424/85.2 |
| 2009/0156882 A1 * | 6/2009 | Chi Sing et al. | 600/7 |
| 2009/0198095 A1 * | 8/2009 | Acosta et al. | 600/3 |
| 2009/0234176 A1 | 9/2009 | Lebovic et al. | |
| 2009/0234177 A1 | 9/2009 | Lebovic et al. | |
| 2009/0234178 A1 | 9/2009 | Lebovic et al. | |
| 2009/0240095 A1 | 9/2009 | Lebovic et al. | |
| 2009/0264696 A1 * | 10/2009 | White et al. | 600/8 |
| 2009/0306453 A1 * | 12/2009 | Popowski et al. | 600/7 |
| 2009/0312593 A1 | 12/2009 | Drobnik | |
| 2010/0048977 A1 * | 2/2010 | Sing et al. | 600/6 |
| 2010/0121129 A1 | 5/2010 | White et al. | |
| 2010/0130807 A1 | 5/2010 | White et al. | |
| 2010/0152519 A1 | 6/2010 | White et al. | |
| 2010/0222628 A1 | 9/2010 | White et al. | |
| 2011/0257459 A1 | 10/2011 | Sutton et al. | |

FOREIGN PATENT DOCUMENTS

| | | |
|---|---|---|
| WO | 2007079278 | 7/2007 |
| WO | 2008112223 | 9/2008 |

OTHER PUBLICATIONS

Pearcey, R., Brundage, M., Drouin, P., Jeffrey, J., Johnston, D., Lukka, H., MacLean, G., Souhami, L., Stuart, G., and Tu, D. "Phase III Trial Comparing Radical Radiotherapy With and Without Cisplatin Chemotherapy in Patients With Advanced Squamous Cell Cancer of the Cervix," 2002, J. Clin. Oncol. 20: 966-972.*

Jolly, S., Vargas, C., Kumar, T., Weiner, S., Brabbins, D., Chen, P., Floyd, W., Martinez, A.A., "Vaginal brachytherapy alone: An alternative to adjuvant whole pelvis radiation for early stage endometrial cancer," Gynecologic Oncology 97 (2005) 887-892.*

PCT, International Search Report and Written Opinion in International application No. PCT/US09/35598, Jul. 6, 2009, 13 pages.

PCT, International Search Report in International application No. PCT/US11/24587, Apr. 6, 2011, 1 page.

Nag et al., "The American Brachytherapy Society Recommendations for Low-Dose-Rate Brachytherapy for Carcinoma of the Cervix," Int. J. Radiation Oncology Biol. Phys., 2002, vol. 52(1), pp. 33-48.

Small et al., "American Brachytherapy Society Survey Regarding Practice Patterns of Postoperative Irradiation for Endometrial Cancer: Current Status of Vaginal Brachytherapy," Int. J. Radiation Oncology Biol. Phys., 2005, vol. 63 (5), pp. 1502-1507.

Yoo et al., "Treatment planning for prostate brachytherapy using region of interest adjoint functions and a greedy heuristic," Phys. Med. Biol. 2003, No. 48, pp. 4077-4090.

* cited by examiner

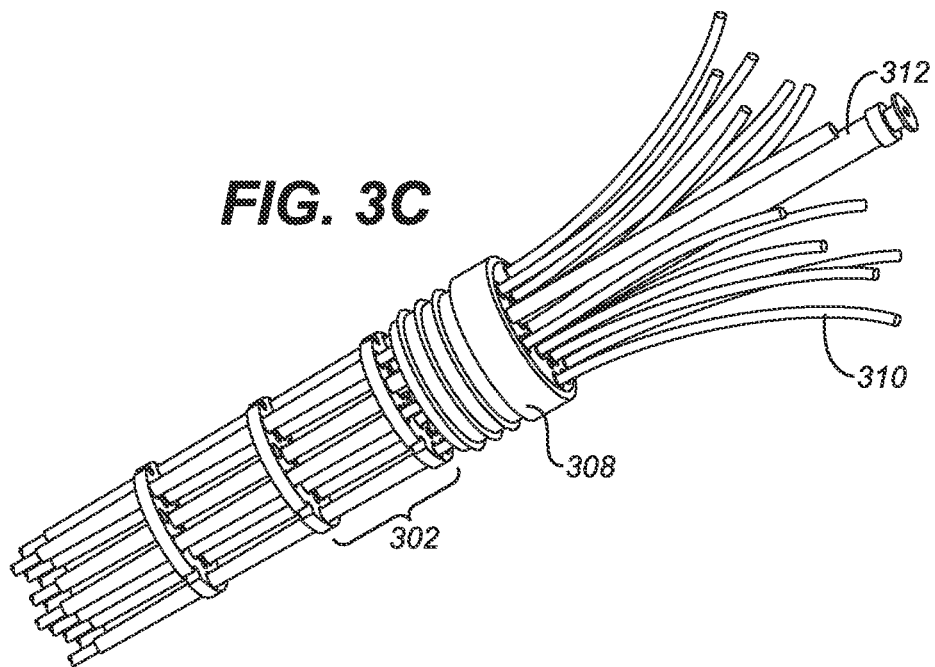
FIG. 3C
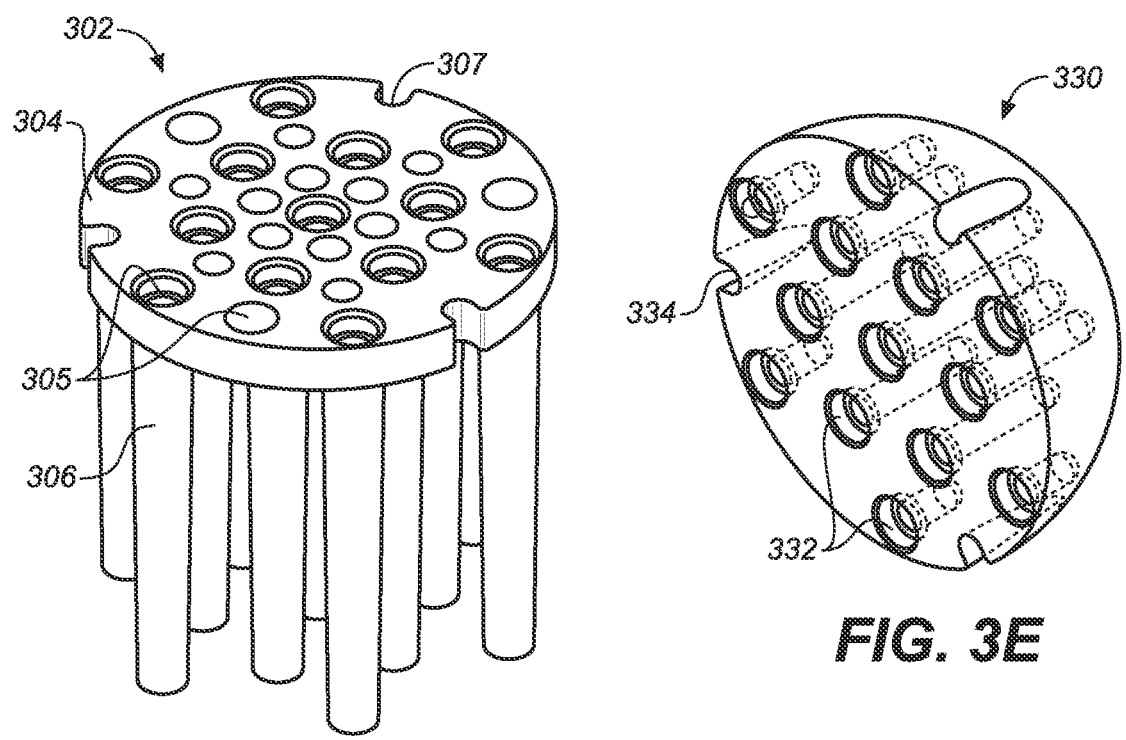
FIG. 3D
FIG. 3E

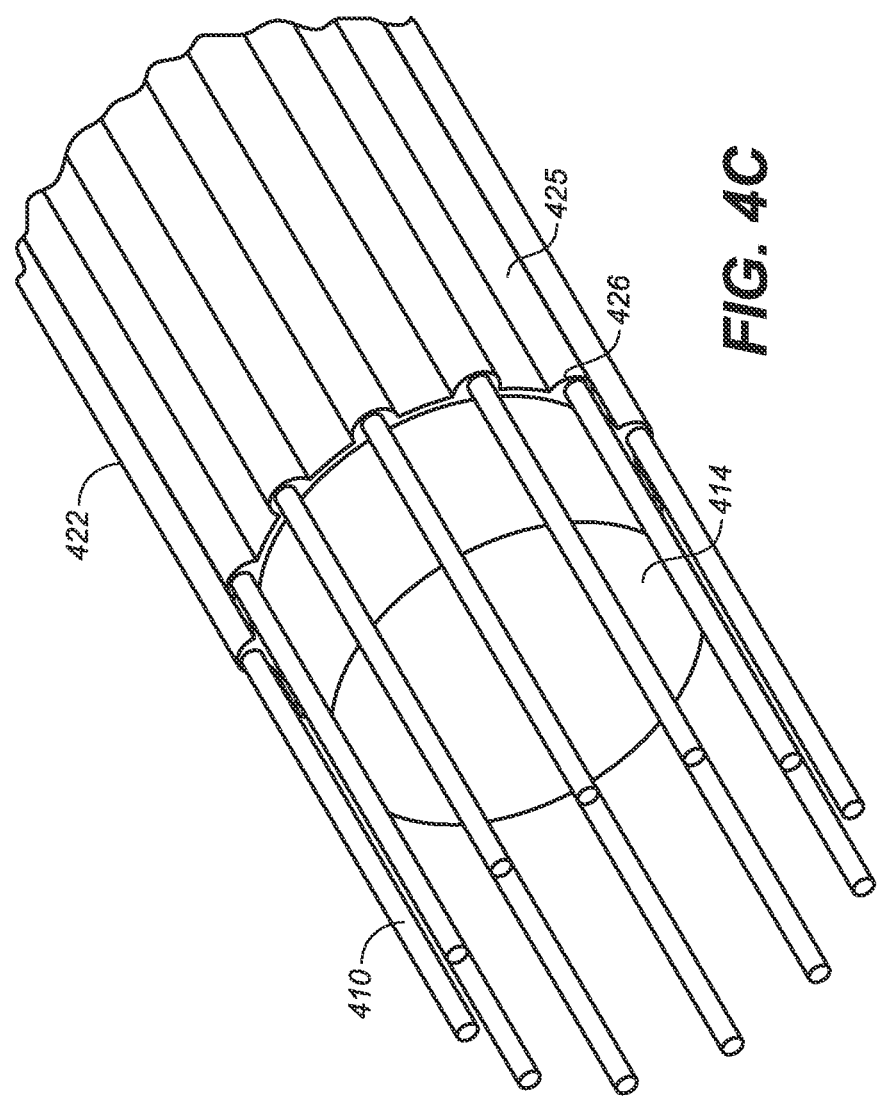

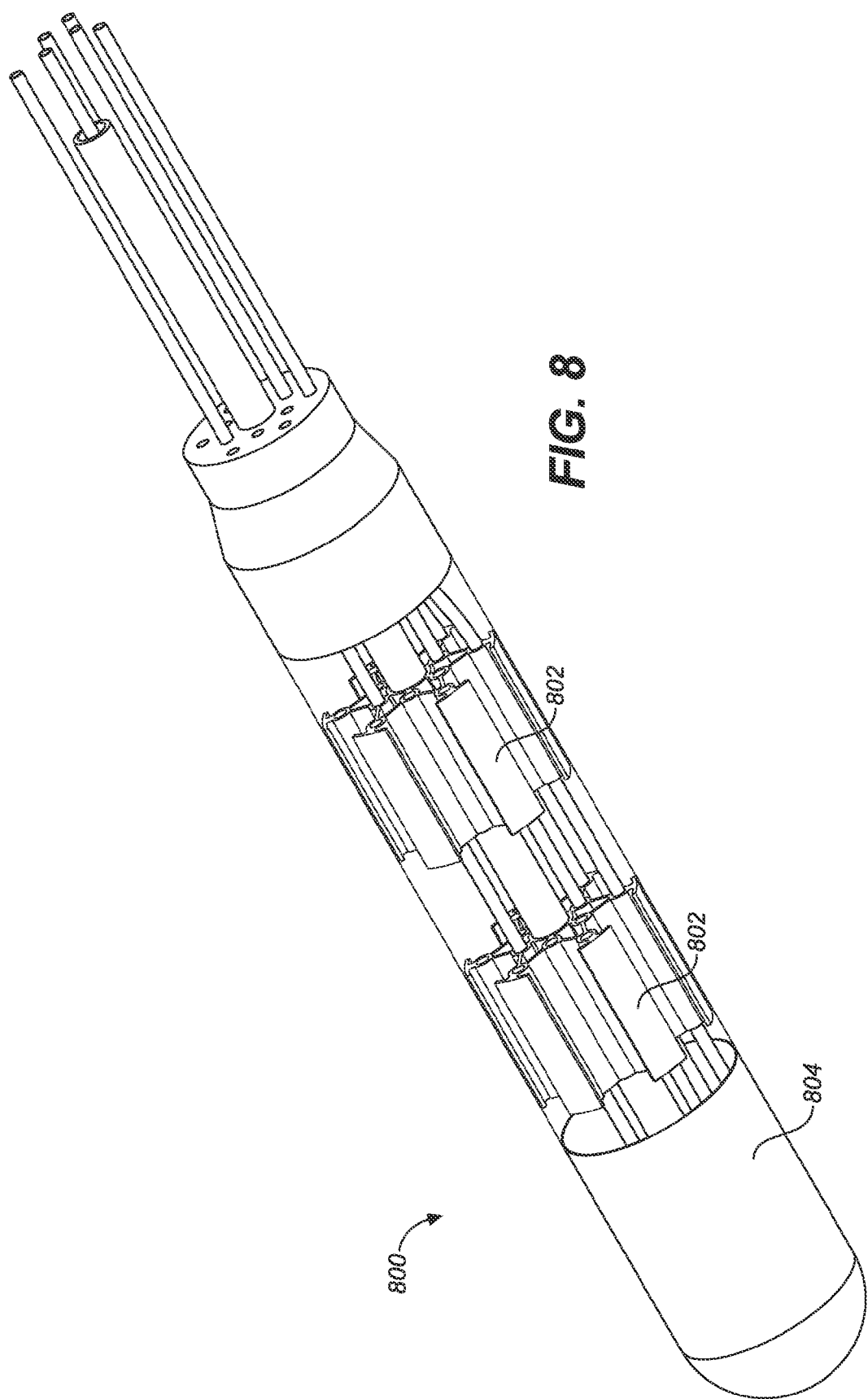

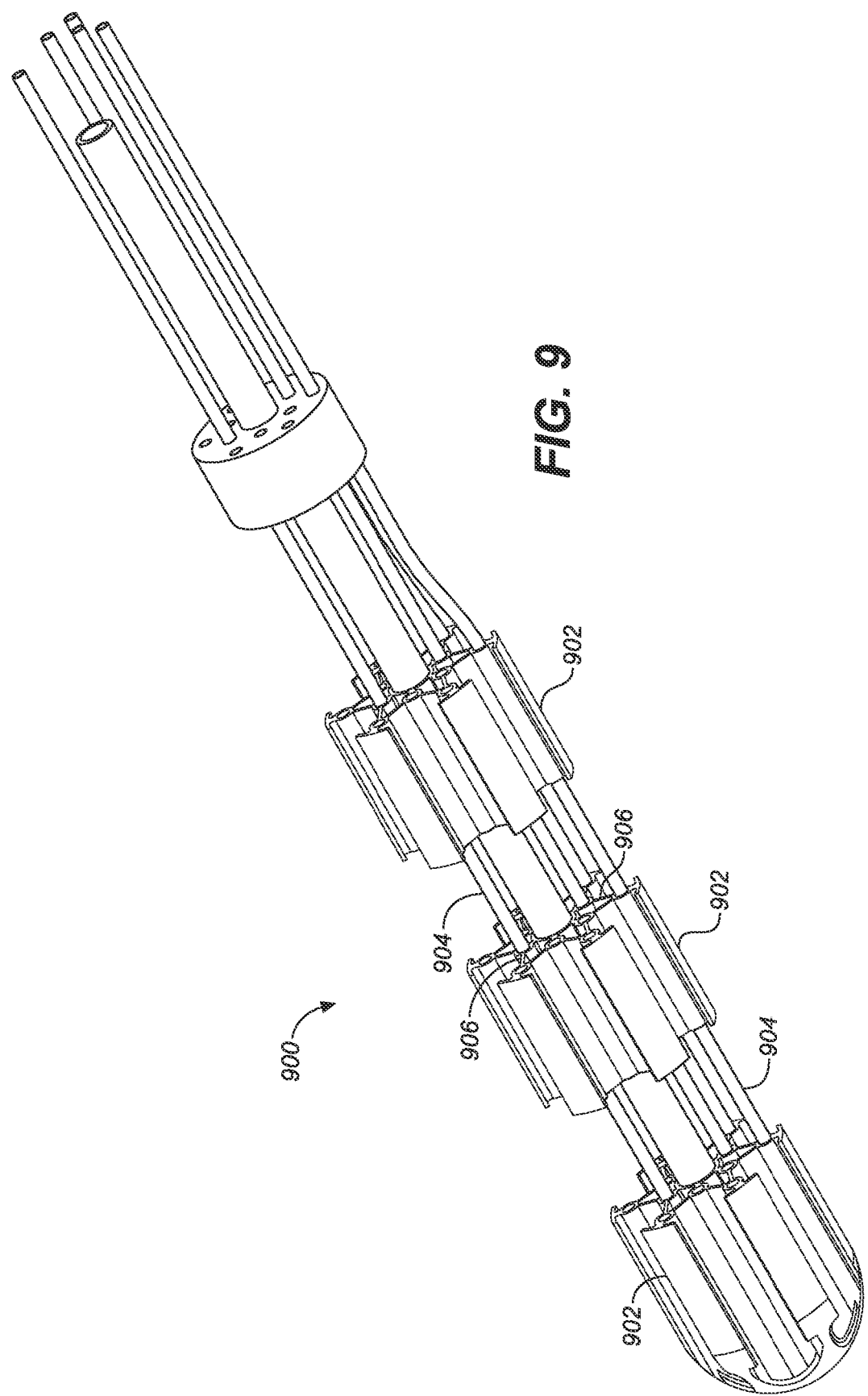

BRACHYTHERAPY APPLICATOR

CROSS-REFERENCE TO RELATED APPLICATIONS

This application claims priority to U.S. Provisional Patent Application Ser. No. 61/304,269 filed on Feb. 12, 2010, which is hereby incorporated by reference in its entirety.

FIELD

Described here are brachytherapy applicators that generally comprise a modular support matrix. The brachytherapy applicators may be flexible or substantially rigid. The brachytherapy applicators may also be radially and/or axially expandable to tailor the fit of the applicators to the surrounding gynecological tissues. Systems and methods for delivering radiation therapy using the brachytherapy applicators are also described.

BACKGROUND

Radiation therapy is used to treat various malignant tumors, either pre-operatively, as adjuvant therapy after surgery, as primary therapy for patients unable to tolerate surgery, or to treat recurrences after surgery. It has been demonstrated in many areas of surgical oncology that adjuvant radiation treatment following tumor resection reduces the likelihood of recurrence of cancer or other proliferative disease. Patients undergoing radiation therapy may receive external beam treatment, brachytherapy, or both.

Brachytherapy is a term used to describe the short distance treatment of cancer with radiation. This type of treatment typically involves placing the radiation directly into or near the tissue to be treated. The radiation dose may then be delivered over a short period of time (temporary implants) or over the lifetime of the source to a complete decay (permanent implants). Treatment is often delivered in fractions spaced in time to take advantage of the fact that normal cells recover from radiation exposure whereas diseased cells do not.

Brachytherapy may be divided into two main classes: intracavitary and interstitial. With intracavitary brachytherapy, the radiation sources are placed within a body cavity close to the affected tissue. In interstitial brachytherapy, the radiation sources are implanted within a volume of tissue. Positioning of the radiation sources is an important aspect of brachytherapy. In order to effectively deliver radiation to the target tissue while helping to minimize exposure (and radiation damage) of surrounding healthy or normal tissue, the radiation sources must be properly positioned during the entire course of treatment.

In early brachytherapy applications, fluid media comprising radioisotopes were used to fill a balloon positioned within a body cavity or organ in order to provide therapeutic radiation. Later it was recognized that spacing the radiation source away from the tissues being treated provided means to deliver the prescribed radiation with reduced likelihood of overdosing normal tissue. This led to filling the balloon with an attenuating medium, often saline solution, and then adding catheters within the balloon in order to position solid isotope sources. Traditional sources are isotopic seeds of, e.g., iridium 192, that are positioned on wires, and which are manipulated within the catheters to deliver the prescribed treatment to the target tissue surrounding the balloon and the treatment cavity.

Conventional applicators typically used for delivery of radiation therapy from within the vagina are generally rigid tubular cylinders that allow transmission of radiation. For example, an exemplary gynecological applicator is the Fletcher-Suit cervical applicator. This applicator consists of a central tube (tandem) and lateral capsules (ovoids or colpostats). The lateral colpostats provide intravaginal positioning while the central tandem traverses the vaginal canal to project into the cervix. Although the Fletcher-Suit applicator has been widely used, maintaining its position in situ can be difficult due to their weight and the difficulty of ensuring a secure connection between the colpostats and tandem. Other brachytherapy applicators have been developed, e.g., the Miami Vaginal Applicator (Nucletron BV, Veenendaal, NL). However, they can be uncomfortable and/or difficult to insert due to their rigidity and incapability of accommodating variations in anatomy, e.g., variations in the size, shape, and orientation of the uterus among patients, or postoperative distortions in anatomy. In addition, the metallic components of these applicators render them poorly suited for CT imaging and subsequent 3D dose planning.

Given the importance of brachytherapy in the treatment of gynecological cancer, brachytherapy applicators having physical and/or functional characteristics that help optimize radiation delivery to target tissues while minimizing exposure to healthy or normal tissues would be useful. Applicators that can be easily and securely positioned within the body would be desirable. Applicators that have multiple source lumens virtually artifact-free under CT imaging that would facilitate 3D dose planning would also be desirable. Additional applicator designs, e.g., applicators capable of being better tailored to gynecological anatomy would also be useful.

SUMMARY

Described here are brachytherapy applicators, and systems and methods for using them to deliver radiation therapy. The applicators may be useful in various locations within the body, e.g., natural or surgically created cavities or spaces, to treat many different types of proliferative conditions, including malignancies. For example, the applicators may be used to deliver radiation therapy to anal, rectal, or pelvic tissues. Use of the applicators to deliver radiation therapy to gynecologic tissues may be beneficial. The applicators may also be used with various imaging modalities. For example, they may be imageable by x-ray, computed tomography, and magnetic resonance imaging modalities.

The brachytherapy applicators described herein generally include an elongate cylindrical body having a proximal end and a distal end. The elongate body may include a modular support matrix having a plurality of source lumens extending at least partially therethrough. As used herein, the terms "modular support matrix" or "modular matrix" refer to a matrix formed from a combination of similar discrete units (e.g., segments, components, etc.), as further described below. It should be understood that the term "lumen" refers to any passage through which a radiation source may be advanced. For example, a lumen may refer to a space defined by a catheter or conduit, the catheter or conduit itself, or a combination thereof, or a predefined space created within the elongate body without the use of a catheter, e.g., a channel formed by the units of a support matrix that extends along the long axis of the elongate body. The lumens may have any suitable configuration. For example, the lumens may be circular, half-circular, spherical, etc.

The modular support matrices may comprise any number of similar discrete units, but in general will comprise at least two similar discrete units. In some variations, the similar discrete units are segments that define a lumen within the elongate body. Here the segments may include a proximal end, a distal end, and a wall extending therebetween. In this variation, a dilator may be slidably coupled to the plurality of segments within the elongate body lumen via one or more mating elements on the segments and the dilator.

In other variations, the similar discrete units are stacking components. The stacking components may be releasably attached or fixedly attached to one another. In one variation, the stacking components include an array of channels and an integrated wall circumferentially disposed around the array. Here the channels of each segment may operably connect to form a plurality of source lumens. Other conduits may also be slidably disposed within the plurality of source lumens formed by the channels. Alternatively, the stacking components may include a base having a plurality of openings and a plurality of members extending from the base. In this variation, the member lumens of one stacking component may connect to the member lumens of another stacking component via the openings in the base to cooperatively form source lumens.

In another variation, the brachytherapy applicators comprise a modular support matrix that includes a plurality of compressible segments. The compressibility of the compressible segments may help with insertion of the brachytherapy applicator into the tissue, space, cavity, etc., that requires treatment, and/or help conform the applicator to the contours of the area to be treated. Compression of the compressible segments may be afforded by the inclusion of hinges within the matrix.

The plurality of compressible segments may comprise a lumen scaffold, an array of channels, and peripheral lumens. Here the lumen scaffold may include any suitable number of extensions to connect the peripheral lumens to the array of channels. In some instances, a single extension of the lumen scaffold connects the peripheral lumens to the array of channels. In other variations, two extensions of the lumen scaffold connect the peripheral lumens to the array of channels.

Any suitable number of source lumens may be included in the elongate body of the applicators described here. For example, the elongate body may include between 4 and 13 source lumens, between 8 and 13 source lumens, or between 10 and 13 source lumens. In some variations, the elongate body comprises 13 or more source lumens. In other variations, the elongate body also includes a central lumen at least partially therethrough.

The plurality of source lumens may be spaced within the elongate body in any suitable manner. For example, they may be spaced about the circumference of the elongate body. The source lumens may be symmetrically spaced within the elongate body, asymmetrically spaced within the elongate body, equally spaced apart in the elongate body, unequally spaced within the elongate body, or combinations thereof. In some variations, the modular support matrix determines the arrangement of the source lumens within the elongate body. The source lumen arrangement may be defined by the particular arrangement of one or more discrete units, e.g., segments or stackable components. The source lumens may also be oriented to run substantially parallel to the long axis of the elongate body, but other suitable configurations are also contemplated. For example, the source lumens may have a curved or splayed configuration within the elongate body.

The modular support matrices may be configured so that the elongate body has an unexpanded configuration and a radially expanded configuration. The elongate body may expand in the axial (longitudinal) direction when the similar discrete units are connected to one another in series. Any suitable characteristic of the modular support matrices, e.g., length, diameter, number of source lumens, etc., may be modified so that the radiation sources may be appropriately positioned to obtain a certain radiation dose and dose profile.

In further variations, a membrane, e.g., a polymer membrane, may substantially surround the elongate body. The membrane may be used to maintain the position of the discrete units upon placement of the applicator within the body or seal against fluid leaks in the instance where an attenuating fluid such as saline is infused into the applicator. One or more of the membrane, central lumen, source lumens, and elongate body, or portions thereof, may be radiopaque, or combinations thereof may be radiopaque. It should be understood that "radiopaque," as used herein, refers to the applicator or components thereof, e.g., the membrane, central lumen, source lumens, elongate body, or portions thereof, being visible by an imaging device, e.g., megavolt or kilovolt x-ray, computed tomography, or magnetic resonance imaging, but not being so prominent that clinically significant artifact is produced.

The applicators may also include a hub at the proximal end of the elongate body. The hub may be of any suitable configuration. In one variation, the hub has a proximal end and a distal end, and a diameter that is larger at the proximal end than at the distal end. Here the larger proximal end may facilitate easier attachment of the afterloader to the applicator. A removable handle may also be attached to the hub. In some variations, a tip comprising a resilient material may also be provided at the distal end of the elongate body. As an alternative to tip-forming the source lumen catheter closed at the distal tip, it is also possible to embed or surround or press against the distal end of a normally open-ended source lumen into an end cap containing an elastomer to form a fluid-tight seal at the end of the source lumen catheters. As another alternative to tip forming to close the distal end of the source lumen catheters, a 2-3 mm length metal or plastic barbed plug may be pressed into the tip of each of the open-ended catheter as well. An array of barbed-ended plugs integrally built into the applicator tip may also be used.

Brachytherapy systems for delivering radiation therapy are also described. In general, the systems may include a plurality of stacking components as described herein, and at least one hub, and in some cases, a handle. The systems may provide the stacking components, hubs, and handles as separate components or preassembled in whole or in part. One or more conduits for slidable advancement within the applicators may also be included. In some variations, an attenuation medium such as saline is included for infusion into the applicator.

In one variation, the brachytherapy system includes a gynecological applicator comprising an elongate cylindrical body having a proximal end, a distal end, and a support matrix. Here the support matrix includes a wall and defines a lumen between the proximal and distal ends. In this variation, the support matrix also has an unexpanded configuration and a radially expanded configuration, a plurality of source lumens within the wall, and one or more dilators for expanding the support matrix.

Methods for using the brachytherapy applicators for delivering radiation therapy to tissues to treat various proliferative conditions are also described. In general, these methods involve inserting a brachytherapy applicator as described herein into a body region, e.g., the vaginal canal, securing and confirming the applicator position, dose planning, and loading a radiation source within the applicator. The dose planning stage may include the insertion of dummy seeds and may also include 3D volumetric dose planning based on CT imaging of the device and surrounding anatomy. The surrounding anatomy may include the tissue within the target tissue (e.g. vaginal submucosa) as well as the organs at risk (e.g., bladder, rectum, urethra, and small bowel).

In some variations, the methods include advancing a gynecological brachytherapy applicator adjacent to a target tissue, where the gynecological brachytherapy applicator comprises an elongate cylindrical body having a proximal end and a distal end, and a modular support matrix having a plurality of source lumens extending at least partially therethrough, and delivering radiation therapy to the target tissue using the brachytherapy applicator. In this variation, the modular support matrix defines an arrangement of the source lumens within the elongate body.

BRIEF DESCRIPTION OF THE DRAWINGS

FIG. 1A illustrates the applicator in an unexpanded configuration, and FIG. 1B illustrates the applicator in a radially expanded configuration.

FIG. 2A illustrates the assembly of the stacking components. FIGS. 2B-2D provide enlarged views of the array of channels within the stacking components shown in FIG. 2A. FIG. 2E is a perspective view of a fluid-tight membrane or sheath surrounding the stacking components and a hemispherical or otherwise blunt tip.

FIGS. 3A-3E depict a further variation of a brachytherapy applicator with a modular support matrix comprised of stacking components. FIG. 3A is a perspective view of the applicator having a sheath surrounding the stacking components. In FIGS. 3B and 3C, the sheath has been removed. FIG. 3D provides an enlarged view of the stacking component used to form the modular support matrix in FIGS. 3A-3C. In FIG. 3E, an exemplary applicator tip is shown.

FIGS. 4A-4C depict another exemplary brachytherapy applicator. FIG. 4A shows a perspective cross-sectional view of the applicator in an unexpanded configuration having source lumens embedded within its wall. FIG. 4B is an enlarged cross-sectional view of the distal portion of the elongate body and the tip of applicator. FIG. 4C is an enlarged view of the proximal portion of the brachytherapy applicator of FIG. 4A with a dilator slidably disposed with the lumen (radially expanded configuration).

FIG. 7B shows a cross-sectional, axial view of one variation of a compressible segment as taken along line A-A (FIG. 7A). FIG. 7C is an expanded view of the compressible segment shown in FIG. 7B. In FIG. 7D, an exemplary compressible segment lacking a surrounding membrane is shown.

FIG. 8 is an exemplary brachytherapy applicator including a membrane surrounding a plurality of compressible segments.

FIG. 9 depicts the brachytherapy applicator of FIG. 8 without a membrane.

DETAILED DESCRIPTION

Figure 1A:
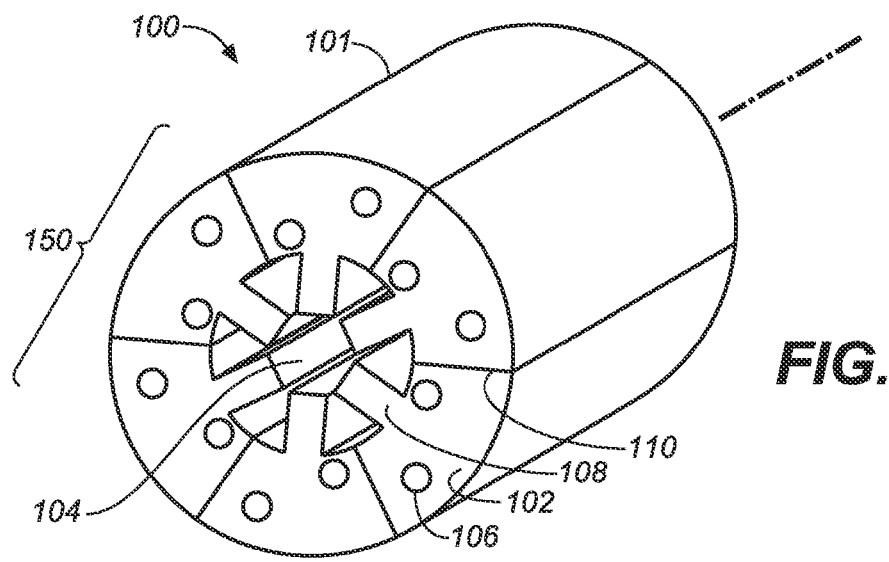
FIGS. 1A and 1B depict expanded views of the proximal end of an exemplary brachytherapy applicator having a modular support matrix comprising radially expandable segments.

Described here are brachytherapy applicators, and systems and methods for using them to deliver radiation therapy. These applicators may comprise a modular support matrix. As further described below, the modular support matrix may be rigid, semi-rigid, or expandable, both radially and axially, or combinations thereof. In some instances, the applicators may be flexible. The modular nature of the support matrix may also help to tailor the dimensions of the applicator to the desired treatment. For example, with these applicators, custom-shaped dose clouds may be provided to help optimize radiation therapy. The dose clouds may be created via CT-based three-dimensional volumetric dose planning software to create a dose cloud covering the target tissue. Any suitable dose cloud configuration that corresponds with a prescribed dose regimen may be generated, keeping in mind to minimize the amount of radiation delivered to healthy or normal tissues.

Any suitable radiation source may be used with the applicators described here. For example, the radiation source may be a radioactive liquid, an x-ray source, a radiation seed, or combinations thereof. More specifically, the radiation sources may comprise without limitation, radionuclides selected from the group consisting of cesium, iridium, iodine, cobalt, palladium, strontium, yttrium, gold, ruthenium, californium, and combinations thereof I. Applicators The brachytherapy applicators described here may have any suitable flexible, rigid, or semi-rigid configuration. In general, the applicators include an elongate cylindrical body having a proximal end and a distal end. The elongate body may include a modular support matrix having a plurality of source lumens extending at least partially therethrough. As previously stated, the term "modular matrix" refers to a matrix formed from a combination of similar discrete units (e.g., segments, components, etc.), as further described below. It should be understood that the terms "discrete units" and "units" are used interchangeably throughout.

The modular support matrices may generally be any structure that defines a suitable array of source lumens within the applicator. The locations of the lumens may be determined as part of the dose planning process, considering also the anatomy of the subject. While the units of certain support matrices may be integrally formed, e.g., unibody construction, other variations of support matrices may be formed of individual modules, segments, or components that are releasably or non-releasably (e.g. bonded, jacketed) connected to one another.

The various modular support matrices may comprise a plurality of individual units that may be assembled together to define an arrangement of radiation source lumens, where the arrangement of source lumens may help to create a radiation dose and radiation dose cloud shape as prescribed by a user. Modular or segmented applicators may be adjustable to suit the clinical needs of the patient. The individual units used within a support matrix may have a substantially similar configuration. The units may be sized and shaped to connect together so that the overall shape of a support matrix may accommodate the target tissues and/or create a certain dose cloud shape. For example, a brachytherapy applicator may comprise an elongate body that has a substantially rounded geometry, with one or more radii of curvature to match the curvature of the target tissue. In some variations, the individual units used to create the support matrix do not connect or contact one another. For example, the units may be spaced along the length of any source lumens that run therethrough.

The components of a brachytherapy applicator may be rigid, semi-rigid, flexible, and/or compressible. The brachytherapy applicators may also be made from materials that are radiopaque, i.e., visible by an imaging device, e.g., x-ray, computed tomography, or magnetic resonance imaging, but not being so prominent that clinically significant artifact is produced. The radiopaque material of the support matrices may also be used to provide slight attenuation of the radiation source. The matrices, when provided in conjunction with the air gaps between the matrices, can create a degree of attenuation of the radiation source that would be roughly equivalent to a water or soft tissue surrounding the radiation source. This attenuation property of the support matrices allows the dose planning software to more accurately depict the actual dose to the surrounding tissue. A membrane may also be included that substantially surrounds the elongate body.

Figure 6:
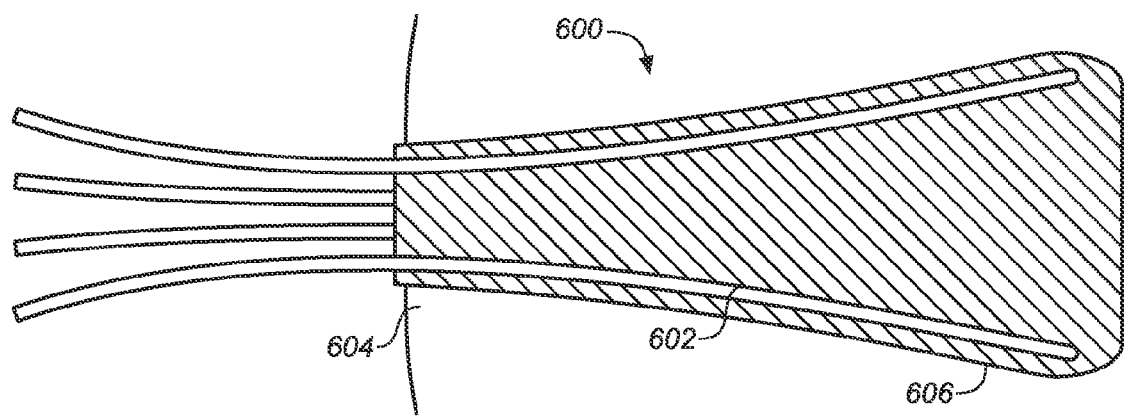
FIG. 6 depicts one illustrative variation of a brachytherapy applicator where the elongate body has a flared distal end.

The elongate body may be of any suitable size, shape, or geometry. For example, the elongate body may be substantially cylindrical or radially asymmetric. With respect to length, the elongate body may be between about 3.0 cm to about 20 cm, between about 3.0 cm to about 15 cm, about 3.0 cm to about 12 cm, about 3.0 cm to about 10 cm, about 3.0 cm to about 8.0 cm, or about 3.0 cm to about 5.0 cm in length. The distal end of the elongate body may be shaped to enhance conformability of the applicator to tissue surfaces and to secure positioning of the applicator during the course of brachytherapy, or to enhance dose shaping ability. In one variation, the distal end of the elongate body is rounded. In another variation, the distal end of the elongate body is flared. For example, as shown in FIG. 6, brachytherapy applicator (600) comprises an elongate body (602) having a proximal end (604) and a flared distal end (606). The flared configuration may be provided, e.g., by an elongate body (602) gradually tapering in diameter from the distal end (606) to the proximal end (604). In further variations, the distal end of the elongate body is flat. In other variations, the distal end may be relatively blunt, tapered, bulbous, ellipsoid, or spherical. One purpose of the elongate body tapering at the distal end of the device is so that the device will better conform to the anatomy. For example, the distal vaginal cavity diameter (e.g., near the introitus) is often smaller than the proximal vaginal cavity diameter near the vaginal cuff. A tapered diameter device will generally be more comfortable to the patient and will provide better dosimetry due to better conformance of the anatomy to the applicator.

Any suitable material may be used to make the elongate body and modular support matrix, so long as the material has the appropriate radiation compatibility and resistance properties. For example, the elongate body may be made from silicones, polyvinylchloride, polystyrene, polycarbonate, latex rubber, and thermoplastic elastomers. The material used to make the elongate body may also be imageable (e.g., visible without creating clinically significant artifact). The ability to image the applicator can be useful in the dose planning process.

The brachytherapy applicators described here may also be configured so that radiation therapy is delivered according to a pre-determined dose cloud shape, making radiation therapy more precise. This may be attributed in part to an elongate body that may include a central lumen extending at least partially therethrough, and one or more source lumens extending at least partially therethrough, and the ability of the elongate body to maintain a relatively preset or predetermined positioning and spacing of the lumens from the outer surface of the applicators. The lumens may be positioned within the elongate body in any suitable manner that delivers the appropriate radiation dose and dose cloud shape to target tissues. As previously stated, a central lumen may run at least partially through the elongate body. In some variations, the central lumen may extend beyond the distal end of the elongate body to serve as a tandem. The central lumen may also be used as an inflation/deflation lumen for passage of fluid into or from the elongate body.

As previously stated, the modular support matrix may define an arrangement of source lumens within the elongate body. The source lumens may be arranged about (around) the circumference of the elongate body or closer to, and around the central lumen, but as previously stated, the lumens may be positioned within the elongate body in any suitable manner that delivers the appropriate radiation dose and dose cloud shape to target tissues. The source lumens may be symmetrically positioned, asymmetrically positioned, equally spaced apart, unequally spaced apart, or any combination thereof within the elongate body. For example, the source lumens may be symmetrically positioned and equally spaced, or symmetrically positioned and unequally spaced. In other instances, the source lumens may be asymmetrically positioned and equally spaced, or asymmetrically positioned and unequally spaced. The source lumens may be spaced from each other a distance of about 1.0 cm to about 5.0 cm. For example, the source lumens may be spaced about 1.0 cm, about 2.0 cm, about 3.0 cm, about 4.0 cm, or about 5.0 cm apart.

In some variations, a material entirely or partially surrounds and extends from the peripheral source lumens, e.g., as a tab, foot, etc. The material helps to keep peripheral source lumens a pre-determined distance from the elongate body outer surface to, e.g., reduce dosimetric hot spots to the immediately adjacent tissue (e.g., vaginal wall mucosa). The distance between the peripheral lumens and elongate body outer surface may be about 2.0 mm, about 3.0 mm, about 4.0 mm, or about 5.0 mm. This distance may in some cases, exceed 5 mm, as long as it is still possible to collapse the applicator to a reduced diameter to facilitate introduction (e.g., through the vaginal introitus) and then expand the applicator to a larger diameter once in position to implement treatment. The material may be a material of any suitable durometer or hardness that maintains the pre-determined distance between the peripheral lumens and the elongate body outer surface, and yet still provides for conformability and flexibility of the adjacent lumens and elongate body. For example, materials such as polymers may be used. Exemplary polymers include without limitation, fluoropolymers, natural and synthetic latex, polyurethane, other thermoplastics, silicone, thermoplastic elastomers, and the like.

The radiation source(s) may also be included in the lumens in any suitable manner that delivers the appropriate radiation dose and dose cloud shape to the target tissues. In one variation, the source lumen(s) contains the radiation source(s) within the elongate body. In another variation, the central lumen contains the radiation source. In some instances, a combination of the central lumen and one or more source lumens contain radiation sources. The central lumen and source lumens may be formed from a flexible polymeric material, e.g., from fluoropolymers, polyetheretherketone (PEEK), polyethylene, polyethylene terephthalate, silicone, polyamides, Pebax® polyether block amide, and the like.

A membrane that substantially surrounds the elongate body may also be provided on the applicators. The membrane may be a flexible film that can be variously secured to the elongate body. In one variation, the membrane is secured to the proximal and distal ends of the elongate body. In another variation, the membrane is attached or secured to the elongate body at one or more intervals along its length. Adhesives such as silicone adhesives and other polymer adhesive well known in the art, or an external elastomer ring may be used to secure the membrane to the elongate body. The membrane may be made from any suitable material that provides the physical strength and elasticity required when using the applicators. Exemplary materials include fluoropolymers, natural and synthetic latex, polyurethane, silicone, thermoplastic elastomers, and the like.

A. Modular Support Matrix: Radially Expandable Segments

Figure 1B:
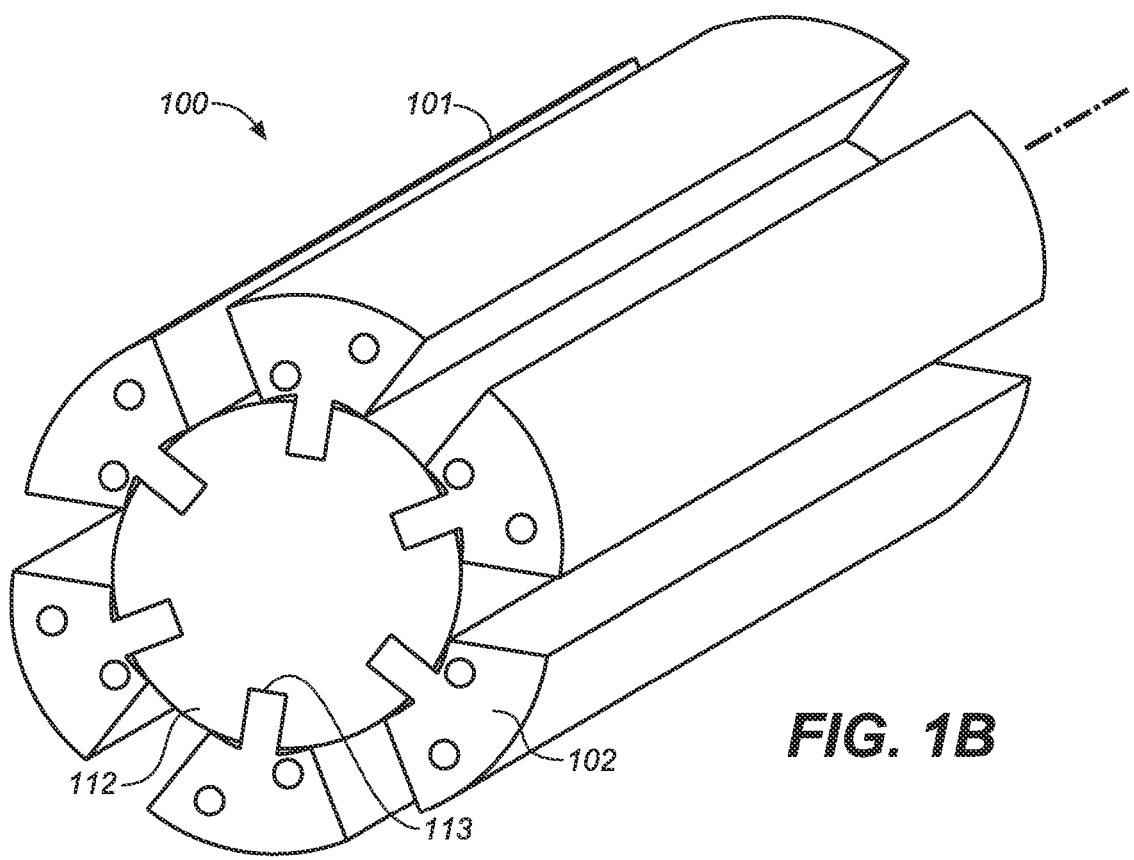

In some variations, the modular support matrix of the brachytherapy applicators is comprised of a plurality of segments. These segments may be configured to provide the elongate body with an unexpanded configuration and a radially expanded configuration. Referring to the figures, FIGS. 1A and 1B show the proximal end of an exemplary applicator (100) comprising an elongate body (101). The elongate body includes a modular support matrix (150) made of segments (102) that extend along the longitudinal axis of the elongate body. The segments (102) may be arranged to form a central lumen (104) of the elongate body (101). One or more source lumens (106) may be placed within the segments (102). The brachytherapy applicator (100) may have a first collapsed or unexpanded configuration, shown in FIG. 1A, and a second radially expanded configuration, shown in FIG. 1B.

The segments (102) may comprise one or more source lumens (106) extending at least partially therethrough. The source lumens (102) may be configured for the passage of conduits or wires having a radiation source (not shown). The source lumens (106) may be arranged with the segments (102) and/or support matrix (150) such that radiation sources advanced therethrough may deliver the desired radiation dose, with the appropriate dose cloud shape. The number and position of source lumens (106) in a segment (102) may be determined in part by the radiation dose and dose cloud shape that is to be applied to the target tissue. For example, the source lumens (106) may be symmetrically or asymmetrically arranged with respect to the central lumen (104). One example of how source lumens may be arranged is shown in FIG. 1A, where each radial segment (102) has two source lumens (106), positioned asymmetrically in the radial segment.

Source lumens (106) may have any shape, e.g., rectangular, circular, elliptical, etc. that may be appropriate for the delivery of radiations sources therethrough. For example, source lumens (106) may be sized and shaped for the passage of a conduit containing a radiation source or a wire with a radiation seed. The source lumens on a given radial segment may have different sizes, shapes and lengths. Neighboring radial segments (102) may have the same or different number and configurations of source lumens (106). In some variations, the source lumen may extend through the entire length of the elongate body (101), i.e., from the proximal end to the distal end, or may extend through only a portion of the length thereof. For example, source lumens (106) may have a length of about 5 cm to about 25 cm.

The individual segments may be sized and shaped to connect with other segments. For example, the segments may have a wall (110) that has contours (e.g., protrusions, grooves, concave/convex curves) that are complementary to the contours of the wall (e.g., grooves, protrusions, convex/concave curves) of neighboring or adjacent segments. These features may help retain the alignment between the neighboring segments. Optionally, the segments may also have a mating element, e.g., a central protrusion (108), where the central protrusions may form the outer perimeter of the central lumen (104). These central protrusions (108) may be configured to also help align the radial segments and/or align or position any devices that may be inserted through the central lumen (e.g., dilators). The segments may be made of any rigid, and/or semi-rigid material, such as polymeric materials, e.g., fluoropolymers, polyetheretherketone (PEEK), polyethylene, polyethylene terephthalate, silicone, polyamides, Pebax® polyether block amide, polyurethane, polyvinyl chloride and the like. The material may also be radiopaque, i.e., visible by an imaging device, e.g., x-ray, computed tomography, or magnetic resonance imaging, but not being so prominent that clinically significant artifact is produced.

The elongate body (101) may have any number of radial segments that may extend along a longitudinal axis of the elongate body, for example, 2, 3, 4, 5, 6, 7, 8, 10, 12, etc. The segments may be retained such that they may move with respect to each other in a concerted fashion (e.g., radially expanding or contracting/collapsing, from a first configuration to a second configuration, etc.), while preserving the general alignment between neighboring segments. For example, the segments of the brachytherapy applicator (100) may be held together by one or more flexible and/or elastic membranes. The membrane may surround the elongate body (101), or may surround and couple a certain number of segments together. The membrane may be made of any suitable material, including without limitation, fluoropolymers, natural and synthetic latex, polyurethane, silicone, thermoplastic elastomers, and the like. The material may also be radiopaque, i.e., visible by an imaging device, e.g., x-ray, computed tomography, or magnetic resonance imaging, but not being so prominent that clinically significant artifact is produced.

Alternatively, the radial segments (102) may be retained together by a system of hinges (e.g., mechanical hinges, living hinges, etc.) that may be actively or passively actuated to move the radial segments, for example, from the first unexpanded configuration (FIG. 1A) to the second radially expanded configuration (FIG. 1B), and vice versa. Hinge mechanisms may be actively actuated by using mandrels, pull cords, push shafts, and the like. Passive hinge mechanisms may be actuated by advancing a device through the central lumen (104), where the device has a larger diameter than the central lumen. The larger diameter of the device that is being advanced through the central lumen may act to expand the applicator, such as is depicted in FIG. 1B. While the brachytherapy applicator (100) shown in FIGS. 1A and 1B is configured to collapse and expand symmetrically in the radial direction, it should be understood that other configurations may be employed. For example, certain variations of brachytherapy applicators may be configured to expand asymmetrically.

The central lumen (104) may have a diameter of about 5 mm to about 20 mm, and/or may any size suited for the device to be advanced therethrough, such as a dilator (112).

The dilator (112) may also include mating elements, e.g., grooves (113), that interlock with the central protrusion (108), which may help to preserve the alignment between neighboring segments (102) and the dilator (112) as the brachytherapy applicator (100) assumes its second radially expanded configuration. Other devices that may be advanced through the central lumen (104) may have similar grooves, protrusions, curves, and surface geometries that may help to maintain the alignment between the radial segments in both the first unexpanded configuration and the second expanded configuration. In the expanded configuration, the source lumens (102) may be arranged such that radioactive sources delivered therethrough may apply the appropriate dose and dose cloud shape to the target tissue. Different dilators may effect varying degrees of expansion, which may in turn affect the delivered dose close shape. The size of the dilator (112) advanced through the brachytherapy applicator (100), the position of radioactive sources delivered through the source lumens, and/or the degree of expansion may be adjusted according to patient anatomy and the desired dose cloud profile.

B. Modular Support Matrix: Stacking Components, Channel Array

Figure 2A:
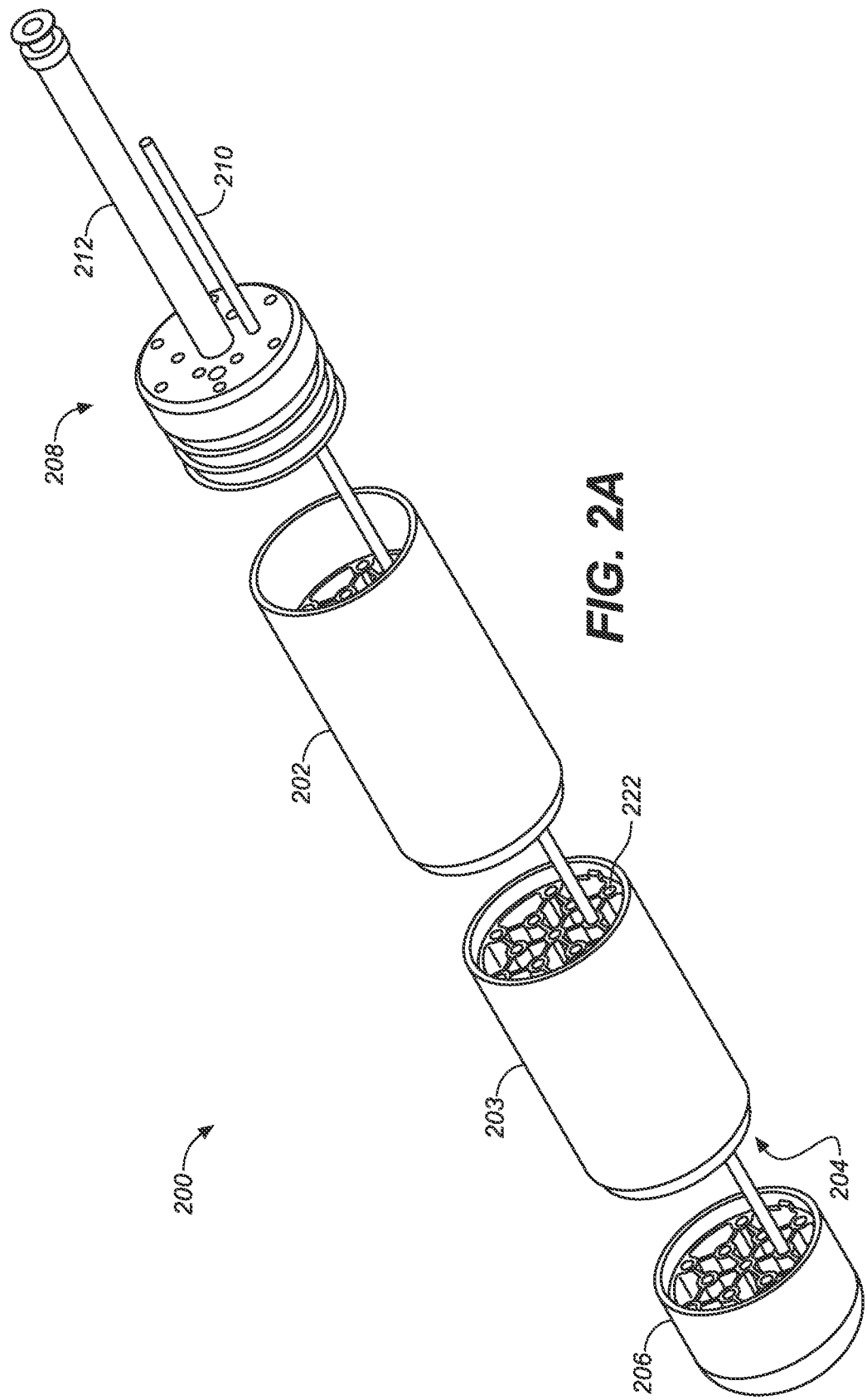
FIGS. 2A-2E show another variation of the brachytherapy applicator that includes a modular support matrix comprised of stacking components.

In another variation, the modular support matrix includes a plurality of stacking components, as shown in the brachytherapy applicator (200) of FIGS. 2A-2E. The stacking components may be releasably or fixedly attached to one another to form the matrix. In FIG. 2A, brachytherapy applicator (200) has a proximal end, a distal end, and a modular support matrix comprising a first stacking component (202), and a second stacking component (203). The support matrix may generally have the shape of an elongate body. A tip (206) may also be provided at the distal end of the elongate body. At the proximal end, a proximal hub (208) may be included.

The brachytherapy applicator (200) may be used with one or more conduits, e.g., source catheter (210) and include a central lumen (212), as shown in FIG. 2A. The hub (208) may comprise one or more openings for the insertion of the central lumen (212) and/or the source catheter (210). The number and arrangement of the openings may be determined in part by the radiation dose and dose cloud shape desired. The hub (208) may have attachment features, such as threads, latches, etc. for connecting to a stacking component. Some variations of the proximal hub may provide additional features for interfacing between the openings and/or lumens within the brachytherapy applicator (200) and any suitable radiation source and/or delivery system (HDR or LDR), for example, various connectors (e.g. luer connectors, transfer cable connectors).

In this variation of the brachytherapy device, each of the stacking components has an integrated wall circumferentially disposed around an array of openings. As shown in FIGS. 2A-2E, the wall circumscribes an array of openings supported by a scaffold. The array of openings may define the configuration of the source lumens within the brachytherapy applicator, while the number of stacking components fitted together may define the length of the source lumens. For example, in FIG. 2A, the first stacking component (202), the second stacking component (203), and the tip (206) may be arranged and aligned such that corresponding openings are lined up. The pathway formed by the aligned openings between the first component (202) and the second component (203) may form a source lumen through which the radiation source catheter (210) may be advanced. In some variations, the source lumen may be substantially continuous from the proximal portion to the distal portion, such that the radiation source catheter (210) may be advanced from the hub (208), through each of the stacking components, into the tip. The configuration of the openings within a series of stacking components may also provide source lumens with different lengths. The stacking components, tip, and/or the proximal hub may be made of a rigid or semi-rigid materials. While the brachytherapy applicator (200) shown in FIG. 2A includes two stacking components, it should be understood that any suitable number of stacking components may be employed. For example, a brachytherapy applicator may have 1, 2, 3, 4, 5, 6, 7 or 8, etc. stacking components, which may be assembled prior to use within a patient. It should also be noted that all segments need not be the same diameter. For example segment (202) may be of smaller diameter than segment (203) so that the diameter of the applicator at the vaginal introitus is less than the diameter deep in the vaginal canal and hence more comfortable for the patient. An intermediate segment (not shown) provides the source lumen transition between the two segments of differing outer diameter.

Figure 2B:
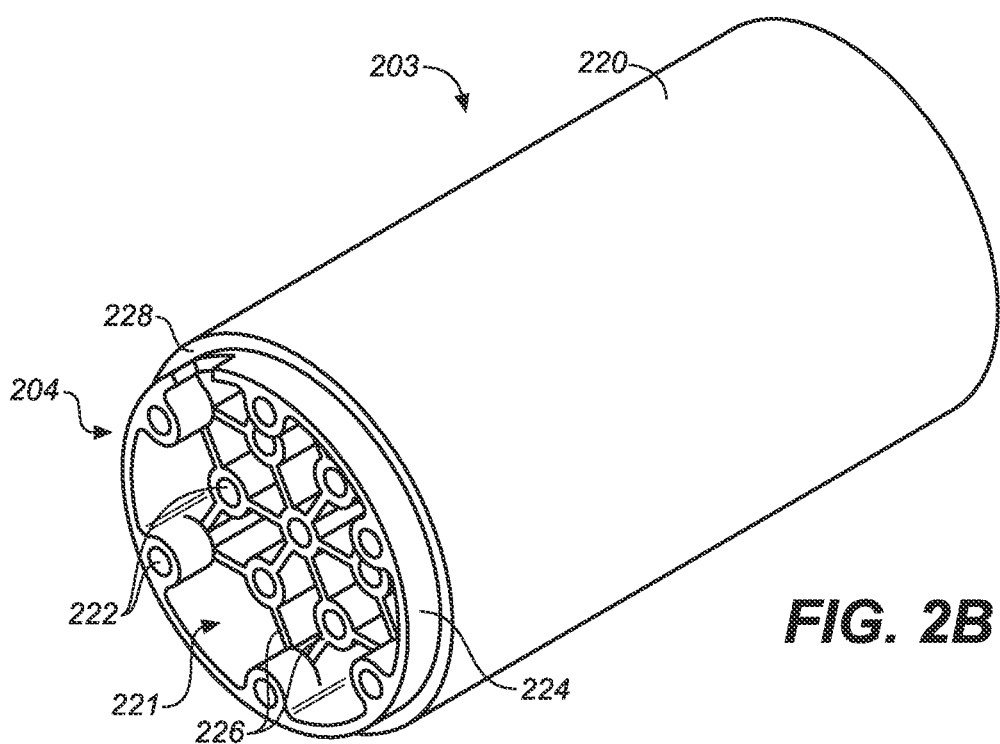
Figure 2D:
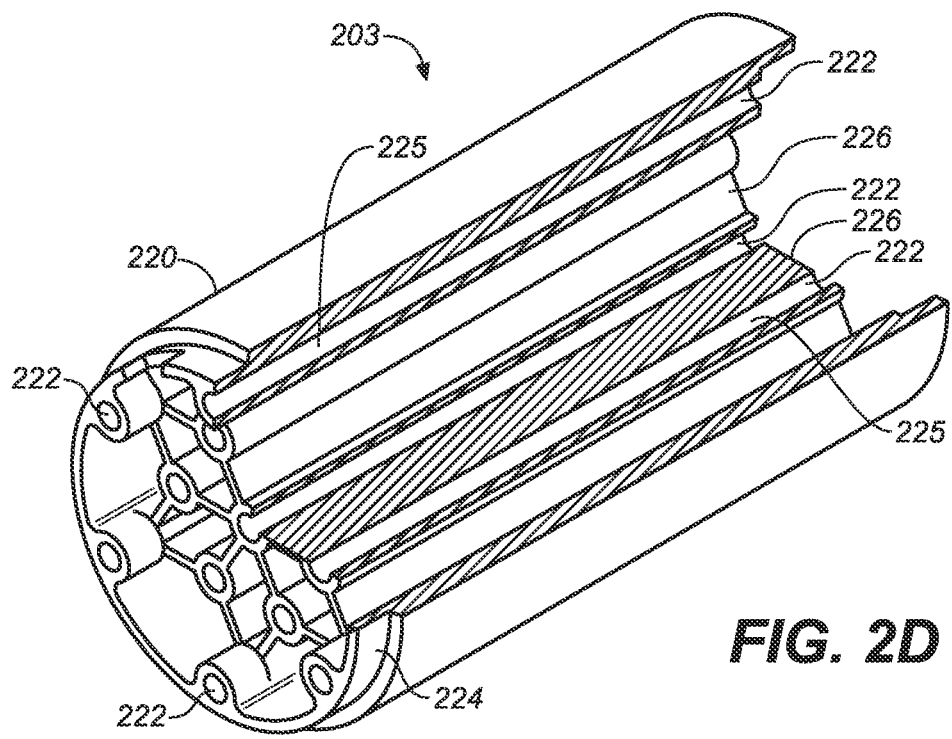
Figure 2C:
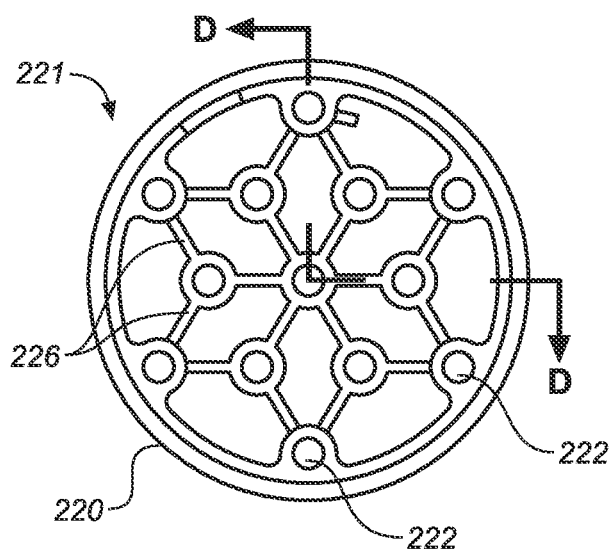

FIGS. 2B-2D depict an exemplary stacking component (203). Stacking component (203) comprises a wall (220) circumferentially disposed around an array of channels. In this variation, the wall (220) may be integrally formed with the matrix (221), but in other variations, the segment wall and the matrix may be fabricated separately and assembled together. The wall (220) may comprise various alignment and attachment features so that multiple stacked components may be connected together. For example, the wall (220) may include an articulating ridge (224), where the articulating ridge (224) is configured to fit into the articulating ridge of an adjacent stacking component. Alternatively, the wall (220) may comprise latches, grooves, hooks, or other features that may facilitate a screw-fit, snap-fit, friction-fit, and the like, between two stacking components. Articulating ridge (224) may also comprise various alignment features, such as a notch (228), which may align one stacking component with an adjacent stacking component in a fixed orientation, e.g., such that individual segments may maintain a certain alignment of matrices, or are restricted from torsioning or rotating with respect to each other. Examples of alignment features that may include corresponding protrusions and grooves, loops and hooks, magnetic components, etc. The stacking component (203) may have any suitable length, for example, from about 2.0 centimeters to about 6.0 centimeters, such as about 2.5 centimeters, or about 5.5 centimeters. The diameter of the stacking component (203) and/or central lumen (204) may be from about 2.0 centimeters to about 4.0 centimeters, for example, about 3.0 centimeters.

FIG. 2C shows a transverse cross-sectional view of the stacking component (203), which shows one variation of the matrix (221). A matrix may comprise an array of channels (225) having openings (222) and a lumen scaffold (226), where the lumen scaffold (226) positions each of the channels (225). The channels (225) may be from about 2 cm to 10 cm in length. In an assembly of multiple stacking components, the collective alignment of the channels may form a pathway for the insertion of radiation sources therethrough. A matrix of such pathways may cumulatively define the arrangement of radiation sources within the brachytherapy applicator, which may shape the dose cloud/profile according to the needs of the patient. The matrix (221) is one example of an arrangement that may be suitable for use with a catheter-based radiation delivery system, but it should be understood that other variations of matrices may be configured to accommodate alternate forms of radiation delivery.

The matrix (221) has 13 openings (222), however, there may be any number of openings, for example, 2, 3, 4, 5, 6, 7, 9, 12, 13, 15, etc., as suitable for the desired radiation dose and dose cloud shape. The openings (222) may be arranged in any configuration according to the lumen scaffold (226), where the lumen scaffold may have any geometry that is structurally suitable. As shown in FIG. 2C, the lumen scaffold (226) is substantially symmetrical, and may be of a radial arrangement, while in other variations, the lumen scaffold may be asymmetrical, and/or the arrangement of the openings (222) may be random. The lumen scaffold (226) may evenly dispose the openings (222) within the matrix, e.g., such that neighboring openings are equidistant, while in other variations, the lumen scaffold may dispose the openings in non-homogeneous clusters. For example, the openings (222) may be arranged concentrically within the central lumen (204), or the openings (222) may be asymmetrically clustered in certain portions of the matrix. The distribution of the openings (222) by the lumen scaffold (226) may be determined in part by the desired radiation dose, dose cloud shape, and/or patient anatomy. One advantage of the stacking matrix design is that the need for contiguous source lumen catheters may be eliminated. As long as the elements are held together securely (e.g., with adhesive or an external enveloping sheath or membrane) the need to fabricate the device from multiple contiguous, and tip formed catheters may be eliminated.

FIG. 2D is a perspective view of a partial cutaway of the stacking component (203), where a radial section of the stacking component is cut away according to the boundary D-D marked in FIG. 2C. As shown here, the channels (225) extend through the entire length of the stacking component (203). In certain variations, the channels may extend through the entire length of the stacking component, while other channels may extend through only a portion of the length, and/or may be capped off.

Figure 2E:
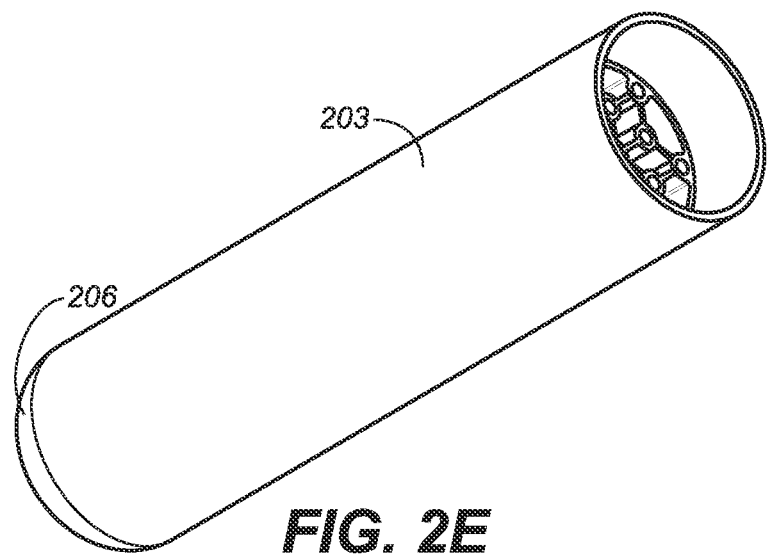

As described previously, individual stacking components may be fit with other stacking components such that a radiation source catheter may be slidably advanced through the pathway formed by the openings. Stacking components may include alignment features as previously described to help ensure that individual openings are aligned. Stacking components may be releasably retained by an elastic and/or flexible membrane, as described above. Stacking components may also be attached to each other using, for example, snap-fit, friction-fit, screw-fit, and other such mechanisms. Similarly, the tip (206) and the proximal hub (208) may have such alignment and attachment features so they may be connected to the stacking components. The number of stacking components that may be attached together may be adjusted by the user to accommodate the anatomy of the patient. For example, FIG. 2E illustrates the stacking component (203) having a tip (206). The tip (206) has a rounded geometry, but it may have any geometry appropriate for approaching the target tissue, and for applying the desired radiation dose and dose cloud shape. For example, the tip may have an elliptical, tapered, spherical, etc., geometry, as appropriate. The stacking components, tip, proximal hub, and the matrices therein may be injection molded or extruded from a variety of thermoplastics such as nylon, polycarbonate, polystyrene or Pebax. The material may be radiopaque, i.e., visible by an imaging device, e.g., x-ray, computed tomography, or magnetic resonance imaging, but not being so prominent that clinically significant artifact is produced.

While the stacking components depicted in FIGS. 2A-2E generally have a circular cross-section, other variations may have different cross-sectional shapes, for example, elliptical, triangular, rectangular, or other polygonal shapes, or may have a custom shape (e.g., shaped as a portion of a curve. U-shaped, spiral-shaped, etc.), which may be tailored according to patient anatomy and the desired radiation dose profile.

C. Modular Support Matrix: Stacking Components, Base with Extending Members

In yet another variation, the stacking components of the modular support matrix include a base having a plurality of openings and a plurality of members having a lumen extending from the base. Such stacking components are shown in the brachytherapy applicator (300) of FIGS. 3A-3E. In those figures, brachytherapy applicator (300) comprises an elongate body (301) with a modular support matrix disposed therein. The modular support matrix may comprise one or more stacking components (302) operably connected to one other to form a source lumen at least partially through the elongate body (301). The stacking components (302) may comprise a base (304) and one or more members (306) extending from the base. An elongate body (301) may also be contained within a sheath (303).

Figure 3A:
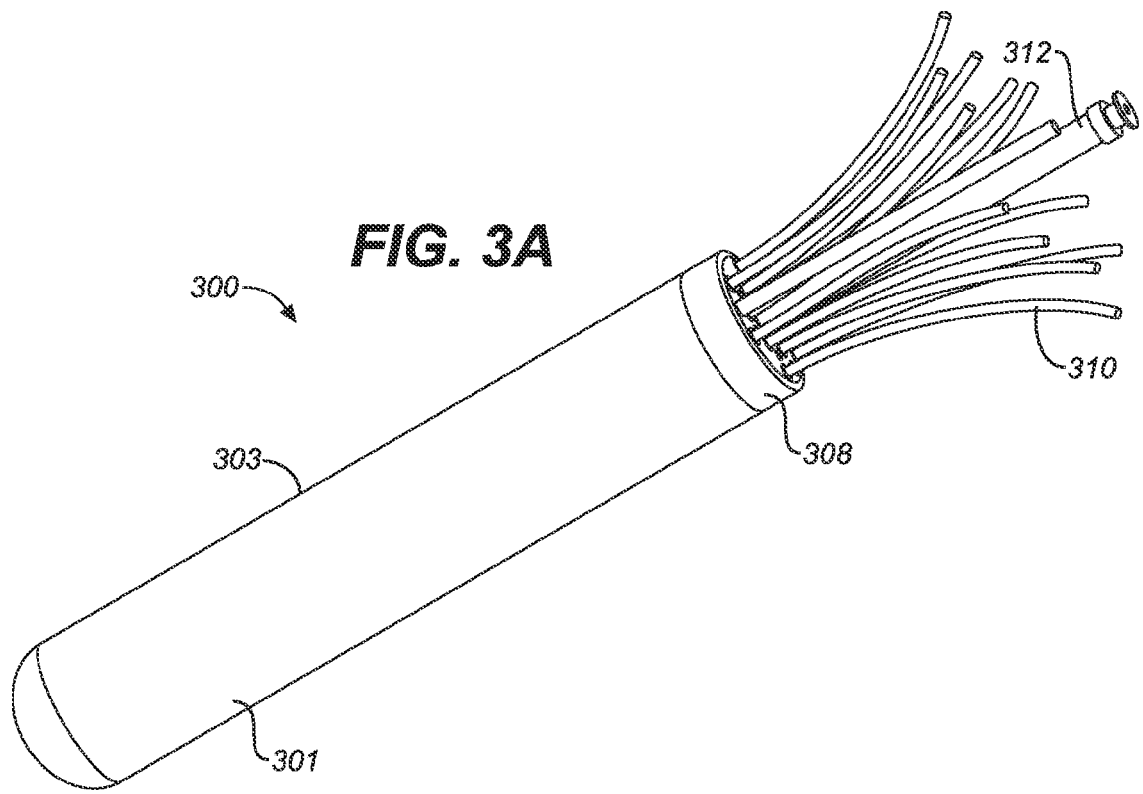
Figure 3B:
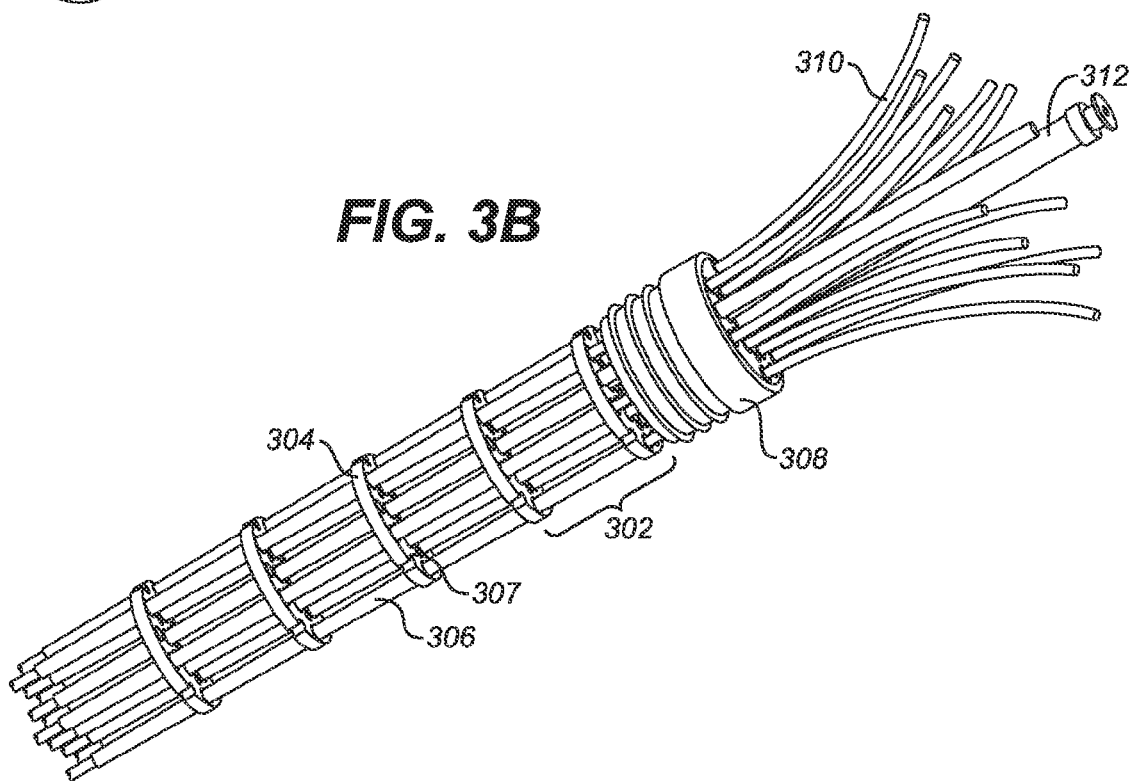

While some variations of stacking components may have a segment wall circumferentially disposed around the support matrix, e.g., stacking components (202, 203), the stacking components (302) may not have a segment wall. Any number of the stacking components (302) may be operably connected to obtain the desired length of the brachytherapy applicator (300), where the desired length may be determined in part by the anatomy of the patient and the suitable dose cloud shape. The support matrix formed by the plurality of stacking components (302) within the elongate body (301) defines an arrangement of lumens through which radiation sources may be positioned, e.g., using source catheter (310). For example, FIG. 3B depicts one variation of the brachytherapy applicator (300) with five stacking components, while FIG. 3C depicts another variation of a brachytherapy applicator with three stacking components. As few or as many stacking components may be connected as needed, e.g., 2, 4, 6, 7, 8, 10, 12, etc.

The proximal portion of the elongate body (301) may comprise a hub (308), configured to interface with one or more radiation source catheters (310) and a central lumen (312). The central lumen may extend all the way through the length of the device so that it forms a pathway for fluids to communicate with the anatomical region near the distal region of the device. This pathway can be useful for instilling contrast media or other liquids into the anatomic region adjacent to the applicator. This pathway can also be used to vent any air or other fluids that may remain in the vaginal cavity as the applicator is inserted into the vaginal cavity. Without this venting feature, trapped air or other fluids may remain around the applicator hindering tissue apposition against the surface of the applicator. These air gaps can compromise the quality of the dose plan that is delivered to the patient. The hub (308) may additionally comprise protrusions and other alignment and/or attachment features, which may help to position, align, and connect the hub (308) with a stacking component. In some variations, hub (308) has a diameter that allows it to attach to sheath (303) via friction fit. As shown in FIGS. 3A-3C, the proximal hub (308) is configured to accommodate 12 source lumens (310)

and 1 central lumen (312). However, any desired number of source lumens are contemplated. The hub (308) may have a port for the infusion of attenuation fluids (e.g., saline).

FIG. 3D depicts an enlarged view of the stacking component (302). The stacking component (302) may comprise one or more openings (305), and one or more notches (307) in and/or around the base (304). There may be any number of openings (305), for example, 6, 8, 10, 15, 18, 20, 24, 28, 30, etc., and the openings may be of any suitable size or shape. Some openings may be circular, rectangular, triangular, hexagonal, etc., and may have a diameter from about 1.5 millimeters to about 5.0 millimeters, for example, 3.0 millimeters, 3.5 millimeters, or 4.0 millimeters. As shown in FIG. 3D, some openings (305) may be in communication with the lumen of member (306), such that a radiation source may be inserted through the opening (305) into the member (306). While members have been shown in FIGS. 3B-3D to be substantially straight with a circular cross-section, it should be understood that they may have any suitable cross-sectional shape as appropriate for the radiation delivery devices to be advanced therethrough. The members (306) may have any suitable length, for example, from about 0.5 centimeters to about 3.0 centimeters, such as 2.5 centimeters. The tubular components on a given stacking component may all have the same lengths, or may have varying lengths.

The openings (305) and the members (306) may be arranged on the base (304) in any suitable manner. In some variations, the distribution of the openings (305) and the members (306) across the base (304) may be homogenous, while in other variations, the distribution may be inhomogeneous. The distribution may be symmetric (e.g., mirror symmetric, radial symmetric, etc.) and/or concentric. The number, shape, and distribution of openings and members may be identical between stacking components, or may vary between adjacent stacking components. The openings and members between two stacking components may be aligned such that a conduit, e.g., a source catheter, inserted through a first opening in a first stacking component may pass through a second opening in a second stacking component, where the second opening is in corresponding alignment to the first opening. Alternatively, the conduit may be inserted through a first opening in a first stacking component, and pass through a second opening in a second stacking component, where the second opening does not correspond to the first opening, or the conduit may be advanced through a first opening in a first stacking component, but be obstructed by the base of the second stacking component. In some variations, the conduit may be advanced through an opening that is in communication with the lumen of a member.

The stacking components (302) may have alignment features, such as notches (307), which may define a certain orientation between adjacent stacking components. In some variations, alignment features such as the notches (307), grooves, protrusions, latches, may have corresponding structures within the lumen wall of the elongate body (301). These alignment features may ensure that the stacking components are assembled in the elongate body (301) with a certain orientation. The types and positioning of various alignment features may be adjusted according to the radiation dose and the dose cloud shape that is desired.

Optionally, some variations of a brachytherapy applicator may have a tip (330), such as is shown in FIG. 3E. The tip (330) may be integrally formed with the elongate body (301), or may be separately fabricated and attached to the distal portion of the elongate body (301) by any appropriate method, e.g., ultrasonic welding, fusing, adhesion, screw-fit, snap-fit, etc. While the elongate body may be made of a substantially rigid or semi-rigid material, the tip (330) may be made of a soft, and/or impressible material, for example, silicone, urethane or various thermoplastic elastomers. This is so that the distal portion of source lumens (331) may be embedded within tip (e.g., to thereby cap or otherwise seal off the open ends of the source lumen catheters. Openings (332) on the tip (300) may also be provided to facilitate embedding and/or positioning of the source lumens. The tip (330) may also have any atraumatic geometry, such as the rounded shape shown here, but may also be elliptical, tapered, and the like. The number, shape, and size (e.g., diameter, length, etc.) of the capped lumens may correspond with the number, shape, and size of the openings (305) and/or the members (306) described above. The tip (330) may also comprise one or more alignment and/or attachment features, such as alignment notch (334), which may help define a certain orientation between the tip and the distal stacking component.

The alignment between the openings and members in different stacking components may collectively form a plurality of pathways for the insertion of radiation sources therethrough. A support matrix of such pathways may cumulatively define the arrangement of radiation sources within the brachytherapy applicator (300), which may shape the dose cloud/profile according to the needs of the patient. For example, as shown in FIGS. 3B and 3C, the arrangement of the openings (305) and the members (306) of each stacking component (302) are substantially identical. The stacking components are arranged such that corresponding openings and members are aligned. Such an arrangement provides substantially straight source lumens, where a radiation source catheter (310) may be advanced from a proximal stacking component, through a first opening, optionally through a member, through a second opening linearly corresponding to the first opening, and so on, through to the distal stacking component, and optionally to the tip. Alternatively, multiple stacking components may be aligned such that some pathways may be longer or shorter than others. The alignment of the openings and the members may be pre-determined and/or fixed according to the radiation dose, dose cloud shape, and the anatomy of the patient. Other variations may allow the alignment of the openings and members to be modified during the procedure, for example, by rotating one stacking component with respect to another. In addition to adjusting the alignment between the stacking components (302), the shape of the elongate body (301) may also be adjusted as desired.

D. Radially Expandable Support Matrix

Figure 4A:
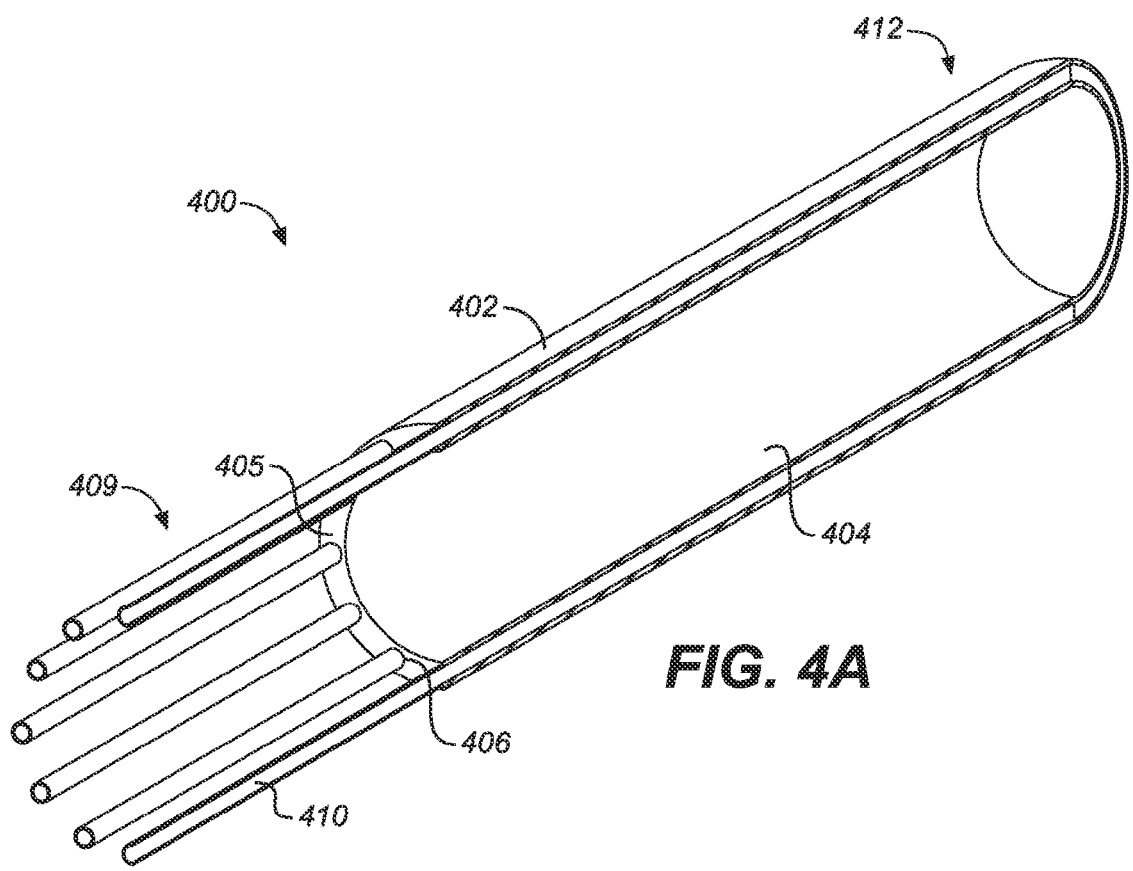
Figure 4B:
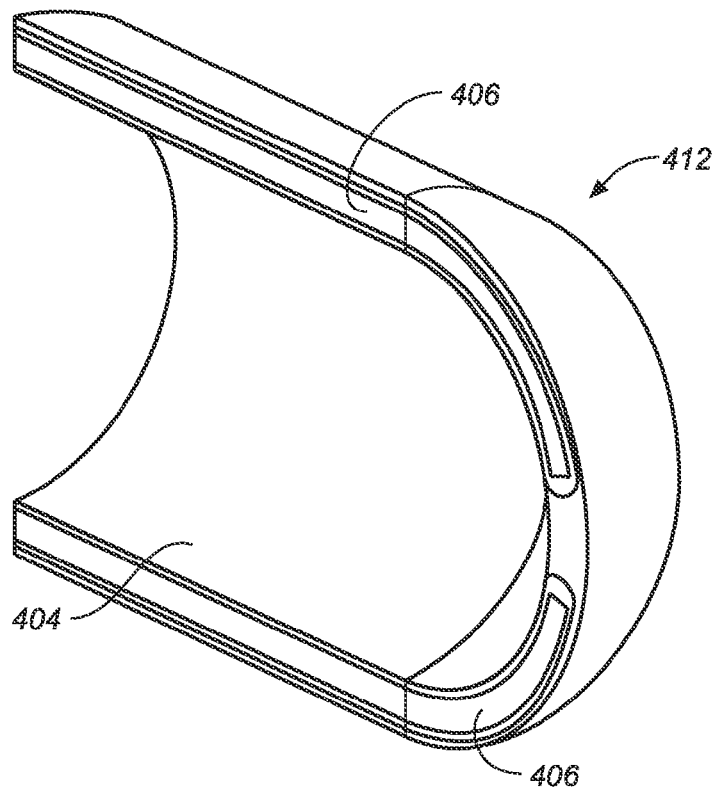

Another variation of a brachytherapy device is depicted in FIGS. 4A-4C. In this variation, brachytherapy device (400) comprises an elongate body (402) with a proximal end (409) and a distal end (412). As shown in FIG. 4A, the support matrix of elongate body (402) includes a wall (405) that defines a lumen (404). The wall (405) comprises one or more source lumens (406) within it, which extend from the proximal end (409) to the distal end (412). The distal end (412) may be shaped to minimize trauma to surrounding tissue upon advancement. The source lumens (406) may be sized and shaped for advancing wires or other conduits containing a radiation source. The elongate body (402) may be made of a semi-flexible material, for example, polyurethane, silicone, or Pebax. The material may be radiopaque, i.e., visible by an imaging device, e.g., x-ray, computed tomography, or magnetic resonance imaging, but not being so prominent that clinically significant artifact is produced. A matrix formed by the wall (405) of the elongate body (402) defines the arrangement of the source lumens within the elongate body (402). Additionally, the lumen (404) of the elongate body (302) may be configured to accommodate one or more devices, for example, additional radiation sources, dilators, fluids, etc.

The brachytherapy applicator may have any number of source lumens, for example, 4, 5, 6, 10, 12, 13, 14, 15, etc. The source lumens may be arranged in any suitable configuration, for example, they may be evenly spaced in the wall (405) as shown, or may be unevenly spaced, or symmetrically or asymmetrically arranged around the circumference of the elongate body. In some variations, as shown in FIG. 4B, the source lumen (406) may follow the general contour of distal end (412). For example, the source lumens (406) may have a curved shape corresponding to the curve of distal end (412). Such a configuration may allow for the delivery of radiation sources to the distal-most portion of the elongate body (402). This may help to deliver radiation therapy to targeted tissue that is not easily accessible, e.g., where the tissue environment is relatively narrow or deep within the body, or where the curvature of the target tissue makes it difficult to precisely position the brachytherapy applicator. For example, the configuration of the source lumens (406) shown in FIG. 4B may be useful for precise application of the radiation dose to the vaginal cuff.

The brachytherapy applicator may have an unexpanded and an expanded configuration. For example, the elongate body may be made of an elastic, flexible, or semi-flexible material, and may be collapsed by rolling or otherwise bunching up the elements into a low profile for insertion. The applicator may be expanded using a dilator and/or a balloon catheter or by filling the lumen (404) with a fluid (e.g., a liquid such as saline). FIG. 4C depicts the proximal portion of the applicator shown in FIG. 4A in a radially expanded configuration. As shown there, a slideably advanceable dilator (414) may be used to urge the elongate body (422) from an unexpanded configuration (e.g. FIG. 4A) to an expanded configuration (e.g., FIG. 4C). The dilator (414) may itself be expanded using a variety of mechanisms, for example, filling with a fluid, such as a gas or liquid, or expanding a mechanical structure by actuating hinges, advancement of a tapered element, and/or relying on super-elastic and/or shape-memory materials. The mechanism used to expand or compress the elongate body may be determined in part by the degree of expansion desired, as well as the anatomy of the patient and the dose cloud shape desired.

E. Modular Support Matrix: Compressible Segments

In another variation, the brachytherapy applicators comprise a modular support matrix that includes a plurality of compressible segments that have an uncompressed and compressed state. The compressibility of the compressible segments may help with insertion of the brachytherapy applicator into the tissue, space, cavity, etc., that requires treatment, and/or help to conform the applicator to the contours of the area to be treated. The material used to make the segments and/or the inclusion of hinges, as further described below, may affect the amount of collapse of the segments when subject to a compressive force (e.g., a collapsing membrane or pressure against tissue).

Figure 7A:
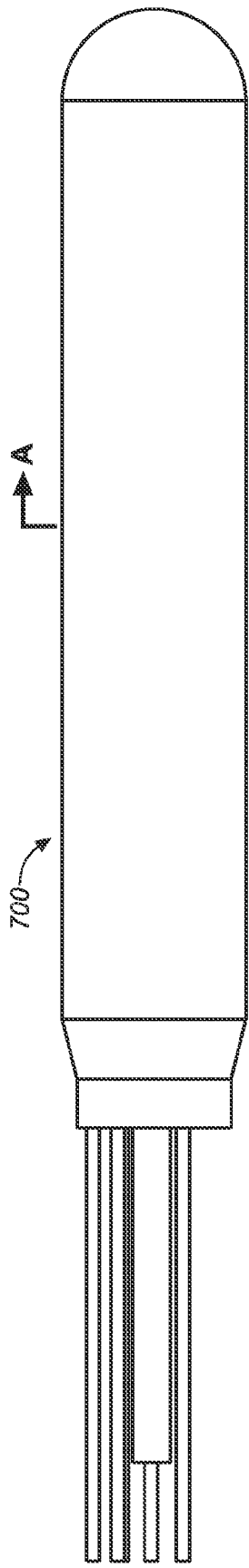
FIGS. 7A-7D show another exemplary brachytherapy applicator including compressible segments.
Figure 7B:
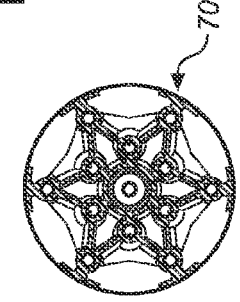

Referring to FIG. 7B, an axial, cross-sectional view of a compressible segment (702) is shown, as taken along line A-A of the applicator (700) depicted in FIG. 7A. An expanded view of the compressible segment (702) in FIG. 7B is shown in FIG. 7C. Compressible segment (702) may include a matrix (704) that is structurally similar to the stacking component matrix (221) shown in FIG. 2C. For example, matrix (704) may comprise an array of channels (706) and a lumen scaffold (708), where the lumen scaffold (708) positions each of the channels (706). The channels (706) and compressible segments (702) may be any suitable length. In some variations, the channels (706) and compressible segments may be from about 2.0 cm to about 10 cm in length. Any suitable number of channels may also be included in the brachytherapy applicators. For example, there may be 2, 3, 4, 5, 6, 7, 9, 12, 13, 15, etc., channels, as suitable for the desired radiation dose and dose cloud shape. Any suitable number of compressible segments may also be included in the brachytherapy applicators.

In an applicator where multiple compressible segments are employed, the collective alignment of the channels may form a pathway for the insertion of source lumens therethrough. A matrix of such pathways may cumulatively define the arrangement of radiation sources within the brachytherapy applicator, which may shape the dose cloud/profile according to the needs of the patient. The matrix (704) in FIG. 7C is one example of an arrangement that may be suitable for use with a catheter-based radiation delivery system, but it should be understood that other matrix configurations may be used. The lumen scaffold may evenly dispose the channels within the matrix, e.g., such that neighboring channels are equidistant, while in other variations, the lumen scaffold may dispose the channels in non-homogeneous clusters. For example, the channels may be arranged symmetrically, or the channels may be asymmetrically clustered in certain portions of the matrix (e.g., along the lateral portions of the device with respect to the patient). The distribution of the channels by the lumen scaffold may be determined in part by the desired radiation dose, dose cloud shape, and/or patient anatomy.

In some variations, the compressible segments include peripheral lumens (710) that have tabs or feet (712). The tabs or feet (712) serve as spacers that help to keep peripheral lumens (710) a pre-determined distance from the elongate body outer surface to, e.g., reduce dosimetric hot spots to the immediately adjacent tissue (e.g., vaginal wall mucosa). The distance between the peripheral lumens and elongate body outer surface may be about 2.0 mm, about 3.0 mm, about 4.0 mm, or about 5.0 mm. This distance may in some cases, exceed 5.0 mm, as long as it is still possible to collapse the applicator to a reduced diameter to facilitate introduction (e.g., through the vaginal introitus) and then expand the applicator to a larger diameter once in position to implement treatment. The tabs or feet (712) may be made from material that is the same or different from the material of the matrix. The material may be a material of any suitable durometer that maintains the pre-determined distance between the peripheral lumens and the elongate body outer surface, and yet still provides for conformability and flexibility of the adjacent lumens and elongate body. For example, materials such as polymers may be used. Exemplary polymers include without limitation, fluoropolymers, natural and synthetic latex, polyurethane, other thermoplastics, silicone, other thermoplastic elastomers, and the like.

A membrane that entirely or substantially surrounds the elongate body including a plurality of compressible segments may also be provided on the applicators. The membrane may be made from any suitable material that provides the physical strength and elasticity required when using the applicators. Exemplary materials include fluoropolymers, natural and synthetic latex, polyurethane, other thermoplastics, silicone, thermoplastic elastomers, and the like. The membrane may be a flexible film that can be variously secured to the elongate body. In one variation, the membrane is secured to the proximal and distal ends of the elongate body. In another variation, the membrane is attached or secured to the elongate body at one or more intervals along its length. For example, as shown in FIG. 7C, the membrane (714) may be secured to the tabs or feet (710) of the compressible segments (702). Adhesives such as silicone adhesives and other polymer adhesives well known in the art may be used, or an external elastomer ring may be used to secure the membrane to the elongate body. In some instances, adhesives are not used, and the membrane itself, due to friction and/or expansion of the compressible segment against the membrane, secures the compressible segment in place along the length of the applicator. A cutaway view of an exemplary brachytherapy applicator (800) comprised of compressible segments (802) and a membrane (804) is shown in FIG. 8. Inflation of the membrane (804) by the instillation of a gas through central lumen (806) may be used to expand brachytherapy applicator (800).

Figure 7D:
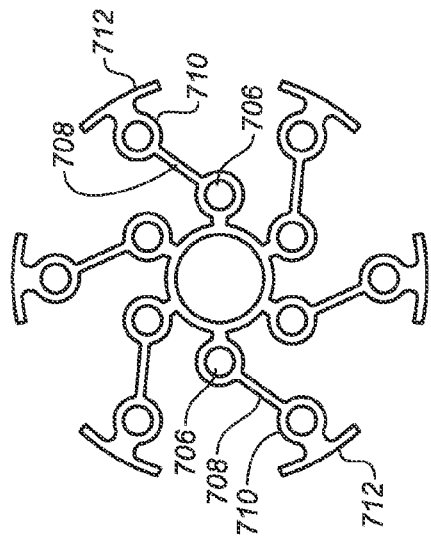
Figure 7C:
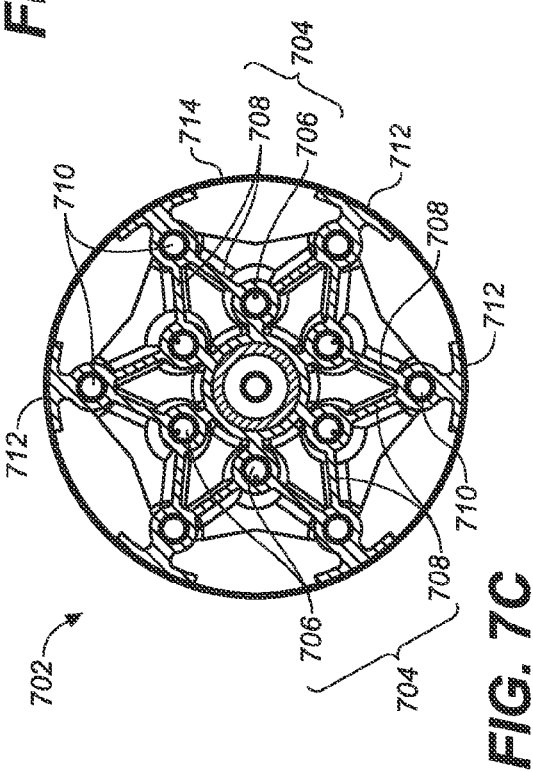

In FIG. 7D, a cross-sectional view of another variation of a compressible segment is shown. Here a membrane does not surround the compressible segment and only one extension of the lumen scaffold (708) is present to connect or contact the peripheral lumens (712) to the channels (706). This differs from FIG. 7C where two extensions of the lumen scaffold (708) are present to connect or contact the peripheral lumens (712) to the channels (706). Given that some of the interconnecting scaffold elements are missing in the compressible segment illustrated in FIG. 7D, this scaffold design may be more compressible (collapsible) than the scaffold design shown in FIG. 7C. More specifically, the missing scaffold elements may enhance compressibility because it allows the outer peripheral lumens (710) to collapse more closely to the inner channels (706).

In a completely assembled device, the optional membrane is attached to the tabs or feet of peripheral lumens so that the outer array of peripheral lumens expands generally symmetrically with balloon inflation. When a membrane is not included, as shown in FIG. 9 (and with the scaffolding design described in FIG. 7C), placement of the compressible segments (902) in the brachytherapy applicator (900) is secured by friction fit of the source lumens (904) running through the channels (906) of the compressible segments.

Figure 10A:
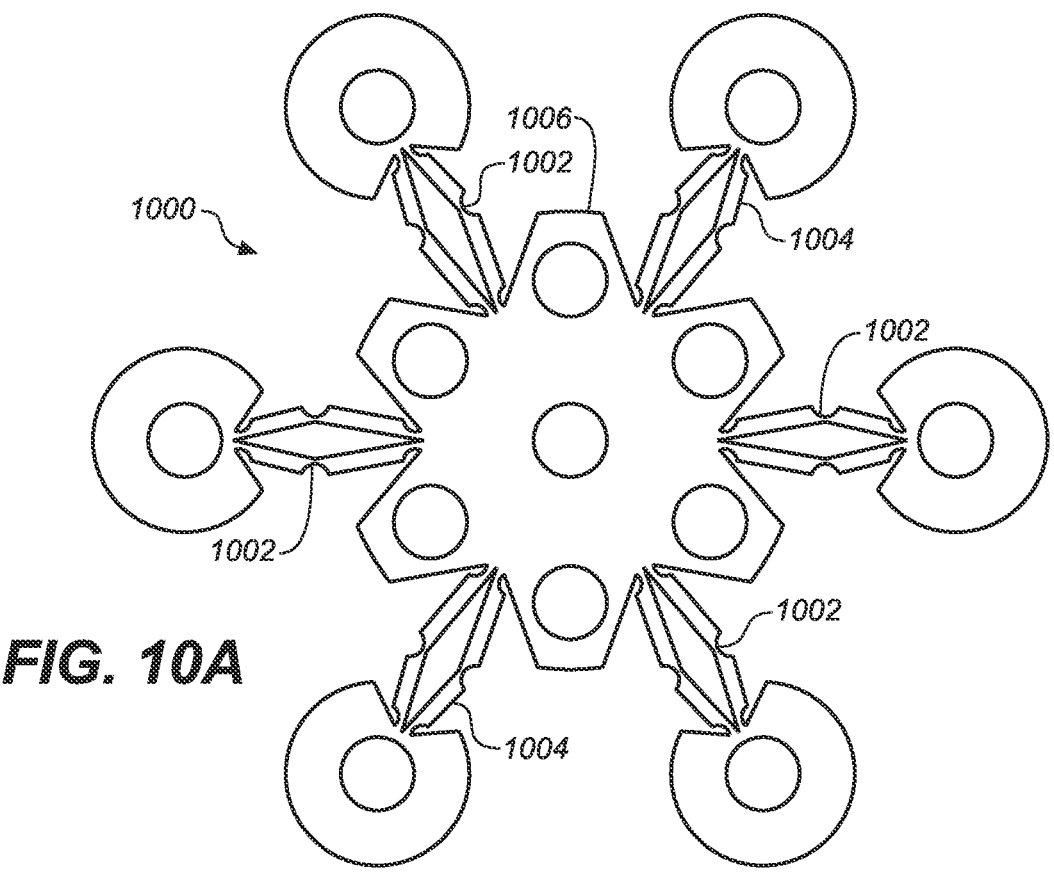
FIGS. 10A-10B show cross-sectional views of exemplary compressible segments having hinges.
Figure 10B:
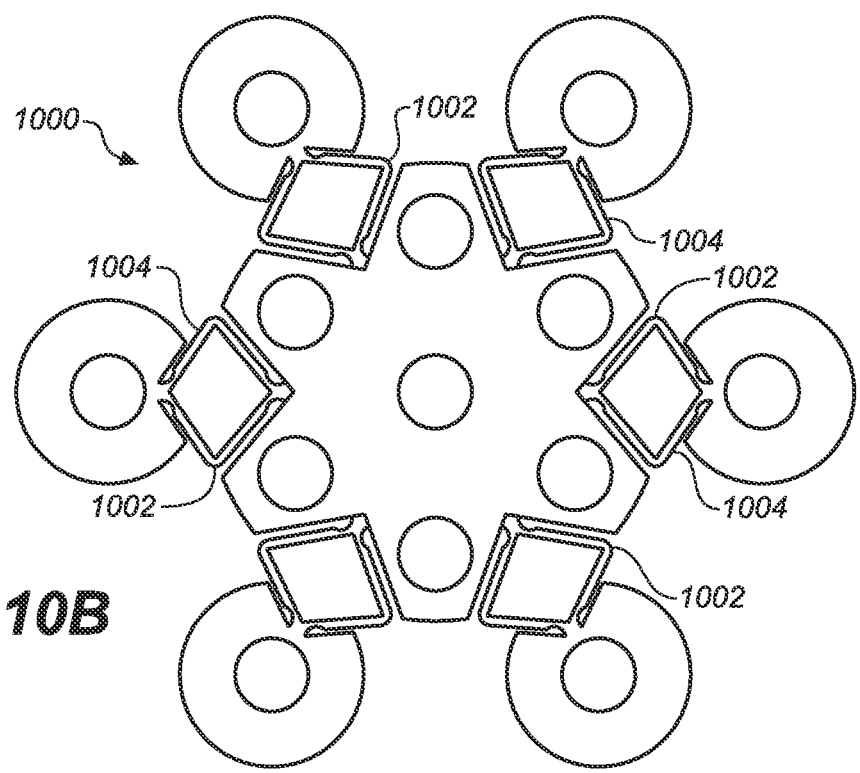

The modular support matrix may include hinges (e.g., living hinges) that may be actuated to move the compressible segments from a first uncompressed configuration to a second radially compressed configuration. For example, as shown in FIGS. 10A-10B, compressible segment (1000) includes a plurality of hinges (1002) within the scaffold (1004) of the matrix (1006). The hinges (1002) are areas of thinner material within the scaffold (1004) that allow bending or flexing along the line of the hinge upon application of a force to at least part of the segment (1000). Other suitable hinge configurations may also be employed. For example, the hinges may be areas of reduced durometer within the scaffold. Force may be applied to the compressible segments, e.g., by a membrane (not shown) that has been collapsed around the applicator. When applied, the force bends the hinges (1002), as shown in FIG. 10B, to compress the compressible segment (1000).

F. Proximal Hub

Figure 5:
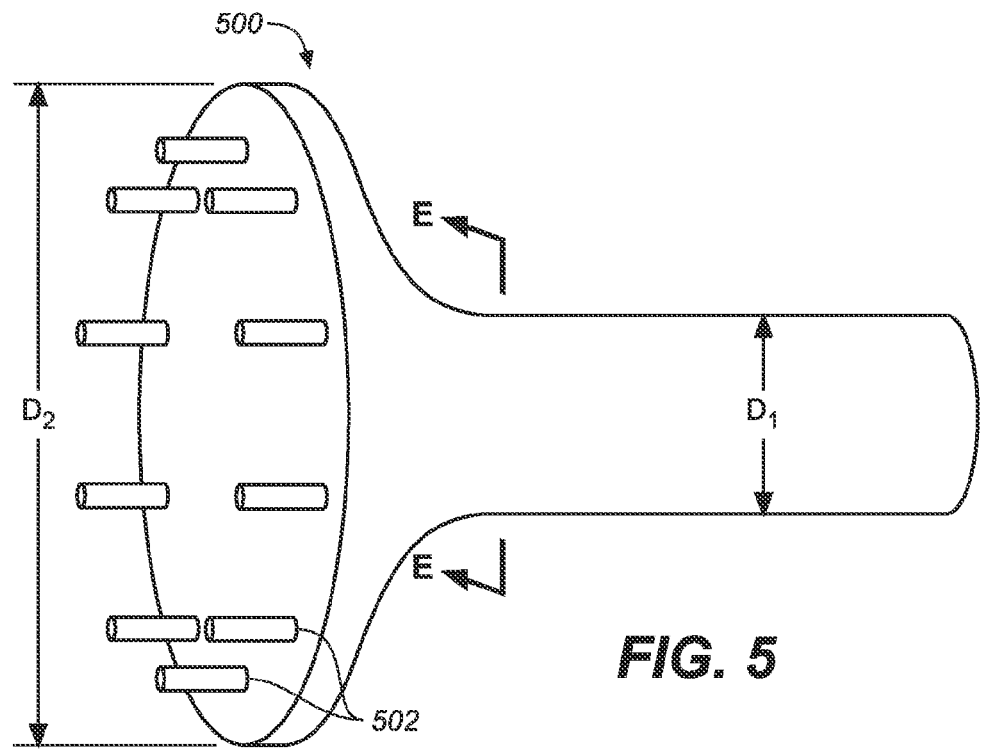
FIG. 5 depicts one variation of a hub that may be used with a brachytherapy applicator.

The overall configuration of the brachytherapy applicators described herein is generally selected so that the applicators approximate the target tissues as closely as possible to provide the prescribed dose of radiation therapy without harming normal tissues. It may also be beneficial to include features that facilitate loading of the radiation sources within the applicator. For example, the hub of the applicator may be configured to facilitate loading of the radiation sources from an afterloader. Referring to FIG. 5, hub (500) is positioned proximal to the proximal end of the applicator (which is designated by the line E-E). Hub (500) includes a proximal end and a distal end, where the distal end has a smaller dimension (e.g., smaller diameter) than the proximal end. Applicator (504) may also have a dimension $D_1$, and the hub (500) may have a dimension $D_2$, where $D_2$ is substantially greater than $D_1$. For example, $D_2$ may be from about 3 cm to about 6 cm. In this variation, the hub having a larger proximal dimension helps facilitate the connection of the afterloader device to the applicator.

The hub (500) may comprise a plurality of source lumens (502). The source lumens (502) may be labeled with numbers or other markings so that the appropriate conduit, wire, etc., may be inserted in a given source lumen. The source lumens (502) may protrude from the hub (500) to thereby further support connection of the afterloader device. Any suitable number of source lumens may be employed, for example, 1, 2, 3, 4, 6, 8, 10, 12, 13, 14, 15, 16, etc., source lumens may be used. The number of source lumens may be determined in part by the desired dose profile.

II. Systems

The brachytherapy systems may include one or more applicators described herein, one or more removable sheaths for housing the applicators during advancement to the target tissue, or one or more handles for advancement and positioning of the applicators. Certain variations of brachytherapy applicators are modular, in which case any number of modules or units may be included in the system, which may allow the user to adjust the size and other characteristics of the applicator according to patient anatomy and/or the desired dose cloud shape. The sheaths that may be included in a brachytherapy system may be of any suitable design so long as the sheaths are capable of housing and supporting the brachytherapy applicator during insertion into the body.

In one variation, the brachytherapy system also includes one or more removable handles for advancement and positioning of the applicators, where the handles may be connected to the hubs described herein. Handles may also be configured to facilitate the delivery of radiation sources into the applicator, as well as to control the infusion of any fluids into the applicator, for example, via a lumen in the hub. Handles may also comprise an electrical interface to allow machine control of radiation source delivery and applicator positioning. For example, a brachytherapy system may also include a computer, which may be used to program the position of applicator, as well as the actuation of radiation source delivery catheters into the applicator to obtain the desired dose cloud shape. Additionally or alternatively, the handle may be manually controlled and actuated.

Variations of a brachytherapy system may also include any number or type of units (e.g., segments or stacking components) that may be assembled to form a suitable applicator. For example, a system may include one or more, e.g., 2, 3, 4, 5, 7, 8, 10, 12, etc., units that may be operably connected to form a desired source lumen support matrix. The units may be identical to each other, or may be different from each other. A variety of tips may also be provided, where the tips may have different shapes, sizes, number of lumens (capped and/or uncapped), etc., and may be made of different materials. Some systems may include a plurality of brachytherapy applicators that vary in length, shape at the distal end, number of openings and/or source lumens. In further variations, the brachytherapy systems may also include dilators or inflation fluid to expand the applicator.

The brachytherapy systems may also include instructions for using the applicators. The instructions may provide information on how to assemble the individual units to form a modular support matrix that arranges the source lumens in a way that address the needs of the patient. Once the applicator has been assembled, the instructions may provide information on how to collapse or expand the applicator, how to insert, advance, or position the applicator in situ, and/or remove the applicator from the body. Furthermore, instructions on how to connect the applicator to an afterloader machine may be provided.

III. Methods

Methods for using the brachytherapy applicators for delivering radiation therapy to tissues to treat various proliferative conditions are also described. The brachytherapy applicators described here may be used in any area of the body that may benefit from radiation therapy. As previously mentioned, the brachytherapy applicators may be used in the pelvis. Specifically, intravaginal, cervical, and intrauterine applications may be useful. In general, these methods involve inserting a brachytherapy applicator into a body region, e.g., the vaginal canal, securing and confirming the applicator position, dose planning, and loading a radiation source within the applicator.

The brachytherapy applicators may be used to treat any body tissue affected by a proliferative condition. Proliferative conditions include tumors, cancers, or other manifestations of abnormal cellular division. For example, the brachytherapy applicators may be used to treat adenocarcinomas, carcinomas, leukemias, lymphomas, myelomas, sarcomas, and mixed-type cancers. Gynecologic cancers such as cervical cancer, uterine/endometrial cancer, ovarian cancer, and vaginal cancer may benefit from treatment with the brachytherapy applicators described herein due their modular and spacing features. Radiation of the vaginal cuff (e.g., after hysterectomy) for endometrial cancer with or without adjuvant pelvic external beam radiation, may also be performed with the applicators described herein. Radiation therapy for proliferative conditions is generally administered over a period of time in partial doses, or fractions, the sum of which comprises a total prescribed dose. For example, about two to about four fractions may be used for vaginal cuff brachytherapy with a total dose of about 10 Gy to about 30 Gy to the target tissue. For cervical cancer, about two to about five fractions may be used with a total dose of about 30 Gy to about 45 Gy to the target tissue. This fractional application takes advantage of cell recovery differences between normal and proliferative tissue, e.g., cancerous tissue, because normal tissue tends to recover between fractions while proliferative tissue tends not to recover or recover at a slower rate.

Treatment planning (dose planning) may occur prior to the initiation of radiation therapy to determine a prescribed dose to be delivered to a volume of the target tissue. In some instances, the prescribed dose may specify a minimum dose to be delivered to a preferred depth outside the treatment cavity (the prescription depth). Other two-dimensional dose prescription regimes are often used as well, e.g., when delivering radiation therapy to the pelvic area. The dose planning process may assess distances from cavity surfaces to skin surfaces or to other radiation sensitive structures (e.g., rectum, bladder, small bowel) and may use these distances in combination with the prescribed prescription depth to determine a dose profile and a dose cloud shape. In this manner, the radiation therapy that is delivered to the target tissue in a subject in need thereof may be configured to provide a pre-determined dose cloud shape. The dose cloud may be of any suitable shape. For example, the dose cloud shape may be symmetric or asymmetric. The modifiable array of spaced source lumens provides for dose planning flexibility. Because of the absence of shielding or any metal components in the applicator, three dimensional volumetric-based dose planning with conventional dose planning software (e.g., supplied by Varian or Nucleotron) may be readily accomplished with these applicators. This approach includes three-dimensional imaging of the cavity or body region of interest, e.g., by computed tomography (CT), magnetic resonance imaging (MRI), or x-ray, and may be automated. With these three-dimensional dose planning systems, dose planning may be performed more precisely and more accurately, and with a greater characterization of the dose that is being delivered to the target tissue as well as adjacent normal tissue structures. This type of three-dimensional dose planning may also automate the dose delivery, thereby improving dosing accuracy and safety.

The brachytherapy applicators may be inserted and advanced in any suitable manner In some variations, the brachytherapy applicators are advanced from outside the body in an unexpanded configuration and advanced to the target tissue. After appropriate positioning, the applicator may then be expanded into its expanded configuration. A sheath may be employed when inserting the brachytherapy applicators, but need not be. When a sheath is used, the brachytherapy applicators may be preloaded in the sheath. Robotic insertion of the applicators described herein is also contemplated.

In some variations, the methods include advancing a gynecological brachytherapy applicator adjacent to a target tissue, where the gynecological brachytherapy applicator comprises an elongate cylindrical body having a proximal end and a distal end, and a modular support matrix having a plurality of source lumens extending at least partially therethrough, and delivering radiation therapy to the target tissue using the brachytherapy applicator. In this variation, the modular support matrix defines an arrangement of the source lumens within the elongate body.

Some brachytherapy applicators may be semi-rigid (i.e., flexible along the long axis but not appreciably deformable in the radial direction), or pre-shaped in different diameters to help reduce any tissue trauma while the applicator is positioned and secured during treatment. In some variations, brachytherapy applicators may be customized according to patient anatomy, which may help facilitate atraumatic placement of the applicator. Certain brachytherapy applicators may have a predetermined geometry that is specifically tailored to accommodate postoperative anatomy, e.g., the anatomy in the proximity of the vaginal cuff. Other brachytherapy applicators may include a plurality of compressible segments as described above.

The radiation sources may then be placed within the brachytherapy applicators by any suitable method. For example, the radiation sources may be afterloaded, either by hand (manual afterloading) or by a machine (automatic remote afterloading) after the brachytherapy applicators are positioned. In other variations, hot loading may be employed. With hot loading, the brachytherapy applicator contains the radiation sources at the time of placement into the subject in need of radiation therapy. The radiation therapy that is subsequently delivered by the radiation sources may provide radiation therapy in a pre-determined dose cloud shape, as previously stated.

The invention claimed is:

1. A gynecological brachytherapy applicator, comprising:
   an elongate cylindrical body having a proximal end and a distal end in a longitudinal axis, the elongate body comprising a modular support matrix comprising a plurality of discreet units having a plurality of source lumens extending at least partially through the plurality of discreet units, and the plurality of discreet units collectively defining an arrangement of the source lumens within the elongate body, wherein the plurality of discreet units are radially expandable, providing the elongate body an unexpanded configuration and a radially expanded configuration;

wherein the plurality of discreet units comprise a plurality of modular segments assembled around the longitudinal axis to collectively define a central lumen, wherein each of the plurality of modular segments has a shape in the unexpanded configuration of the elongate body and retains the shape in the radially expanded configuration of the elongate body.

2. The gynecological brachytherapy applicator of claim 1, wherein the plurality of discreet units comprise a plurality of segments having a similar configuration.

3. The gynecological brachytherapy applicator of claim 2, wherein the plurality of modular segments are held together by one or more flexible membranes in the radially expanded configuration of the elongate body.

4. The gynecological brachytherapy applicator of claim 3, wherein the membrane comprises a polymer.

5. The gynecological brachytherapy applicator of claim 4, wherein the polymer is selected from the group consisting of fluoropolymers, natural and synthetic latex, polyurethane, silicone, and combinations thereof.

6. The gynecological brachytherapy applicator of claim 2, wherein the elongate body has an unexpanded configuration and a radially expanded configuration.

7. The gynecological brachytherapy applicator of claim 6, wherein the plurality of segments define a lumen within the elongate body, each of the segments comprising an elongate segment body having a proximal end, a distal end, and a wall extending therebetween.

8. The gynecological brachytherapy applicator of claim 7, wherein at least two or more of the plurality of source lumens are symmetrically arranged within the elongate segment body relative to the longitudinal axis.

9. The gynecological brachytherapy applicator of claim 7, wherein at least two or more of the plurality of source lumens are asymmetrically arranged within the elongate segment body relative to the longitudinal axis.

10. The gynecological brachytherapy applicator of claim 1, further comprising a dilator configured to engage with the plurality of modular segments in the central lumen to allow the elongate body to radially expand, wherein the plurality of segments and the dilator each comprise one or more mating elements, and the mating elements of the plurality of segments comprising central protrusions defining an outer perimeter of the center lumen.

11. The gynecological brachytherapy applicator of claim 1, wherein the applicator further comprises a central lumen extending at least partially through the elongate body.

12. The gynecological brachytherapy applicator of claim 1, wherein the applicator further comprises a hub at the proximal end of the elongate body, the hub having a proximal end and a distal end, and a proximal end diameter and a distal end diameter.

13. The gynecological brachytherapy applicator of claim 12, wherein the diameter of the hub proximal end is larger than the diameter of the hub distal end.

14. The gynecological brachytherapy applicator of claim 1, wherein the applicator further comprises an applicator tip at the distal end of the elongate body.

15. The gynecological brachytherapy applicator of claim 14, wherein the applicator tip comprises an impressible material.

16. The gynecological brachytherapy applicator of claim 15, wherein the source lumens have a distal portion embedded within the impressible material.

17. The gynecological brachytherapy applicator of claim 1, wherein the modular support matrix comprises a polymer selected from the group consisting of silicones, polyvinylchloride, latex rubber, polystyrene, and polyurethane.

18. The gynecological brachytherapy applicator of claim 1, wherein the distal end of the elongate body is flared.

19. The gynecological brachytherapy applicator of claim 1, wherein the applicator further comprises a radiation source.

20. The gynecological brachytherapy applicator of claim 19, wherein the radiation source comprises source selected from the group consisting of a radioactive liquid, an x-ray source, a radiation seed, and combinations thereof.

21. The gynecological brachytherapy applicator of claim 19, wherein the radiation source comprises radionuclides selected from the group consisting of cesium, iridium, iodine, cobalt, palladium, strontium, yttrium, gold, ruthenium, californium, and combinations thereof.

22. The gynecological brachytherapy applicator of claim 1, wherein the elongate body comprises between 5 and 13 source lumens.

23. The gynecological brachytherapy applicator of claim 22, wherein the elongate body comprises between 8 and 13 source lumens.

24. The gynecological brachytherapy applicator of claim 22, wherein the elongate body comprises between 10 and 13 source lumens.

25. The gynecological brachytherapy applicator of claim 22, wherein the elongate body comprises 13 source lumens.

26. The gynecological brachytherapy applicator of claim 1 wherein the plurality of discreet units are rigid.

27. The gynecological brachytherapy applicator of claim 1 wherein the plurality of discreet units are semi-rigid.

28. A gynecological brachytherapy applicator, comprising:
  an elongate cylindrical body having a proximal end and a distal end and comprises a plurality of discreet units having a plurality of source lumens extending at least partially through the plurality of discreet units, and the plurality of discreet units collectively defining an arrangement of the source lumens within the elongate body;
  wherein the plurality of discreet units comprise a plurality of stacking components connected in a series, defining a longitudinal length of the elongate cylindrical body;
  wherein each of the stacking components has a cylindrical configuration and comprises an array of channels, a scaffold structure positioning the array of channels, and an integrated wall in the cylindrical configuration circumferentially disposed around the array of channels, and
  wherein the integrated walls of the plurality of stacking components are releasably connected to one another in series wherein the channels of each stacking component operably connect to form the plurality of source lumens.

29. The gynecological brachytherapy applicator of claim 28, wherein the plurality of stacking components are releasably attached to one another.

30. The gynecological brachytherapy applicator of claim 28, further comprising at least one conduit slidably disposed within the plurality of source lumens.

31. The gynecological brachytherapy applicator of claim 28, wherein the stacking components comprise a base having a plurality of openings and a plurality of members having a lumen extending from the base.

32. The gynecological brachytherapy applicator of claim 31, wherein the member lumens of one stacking component are connected to the member lumens of another stacking component via the openings in a base to cooperatively form source lumens.

33. A brachytherapy system, comprising: a plurality of stacking components, at least one hub, and at least one removable handle,
wherein each of the stacking components has a cylindrical configuration and comprises an array of channels, a scaffold structure positioning the array of channels, and an integrated wall in the cylindrical configuration circumferentially disposed around the array of channels, and wherein the integrated walls of the plurality of stacking components are releasably attached to one another in series, defining a longitudinal length of the brachytherapy system, wherein channels of each stacking components operably connect to form a plurality of source lumens.

34. The brachytherapy system of claim 33, wherein the system further comprises one or more tips.

35. The brachytherapy system of claim 33, wherein the system further comprises one or more slidably advanceable conduits.

36. A gynecological brachytherapy applicator, comprising:
an elongate cylindrical body comprising a plurality of elongate compressible segments each having a length, an array of channels extending longitudinally and continuously along the length of the plurality of elongate compressible segments and supported by the plurality of elongate compressible segments, and a plurality of peripheral lumens extending longitudinally and continuously along the length of the plurality of elongate compressible segments and supported by the plurality of elongate compressible segments,
wherein the plurality of compressible segments provide the applicator a compressed state for advancement of the applicator to a target tissue and an uncompressed deployed state, and each of the plurality of compressible segments comprises a lumen scaffold connecting the plurality of peripheral lumens to the array of channels.

37. The gynecological brachytherapy applicator of claim 36, wherein the lumen scaffold comprises a hinge.

38. The gynecological brachytherapy applicator of claim 36, wherein the lumen scaffold has a single-extension configuration connecting the peripheral lumens to the array of channels.

39. The gynecological brachytherapy applicator of claim 36, wherein the lumen scaffold has a multi-extension configuration connecting the peripheral lumens to the array of channels.

40. A brachytherapy system comprising:
a gynecological applicator, the applicator comprising an elongate cylindrical body having a proximal end, a distal end, and a support matrix, the support matrix comprising a wall having a length extending continuously between the proximal and distal ends of the elongate cylindrical body and defining a lumen between the proximal and distal ends, wherein the wall has an unexpanded configuration and a radially expanded configuration, and a plurality of source lumens embedded within the wall and extending longitudinally and continuously along the length of the wall; and
wherein the wall is constructed from an elastic material and the plurality of source lumens are received by the elastic material constructing the wall.

41. The brachytherapy system of claim 40, wherein the plurality of source lumens are symmetrically spaced within the wall relative to a longitudinal axis of the elongate cylindrical body.

42. The brachytherapy system of claim 40, wherein the plurality of source lumens are asymmetrically spaced within the wall.

43. The brachytherapy system of claim 40, further comprising a radiation source.

44. The brachytherapy system of claim 40 wherein the wall of the support matrix includes an end portion having a curved contour, and the plurality of source lumens within the wall have a section of a curved shape generally corresponding to the curved contour of the end portion.

45. A method for delivering radiation therapy to a gynecological tissue comprising:
advancing a gynecological brachytherapy applicator adjacent to a target tissue, the gynecological brachytherapy applicator comprising an elongate cylindrical body having a proximal end and a distal end, the elongate body comprising a modular support matrix comprising a plurality of discreet units having a plurality of source lumens extending at least partially through the plurality of discreet units, and the plurality of discreet units collectively defining an arrangement of the source lumens within the elongate body, wherein the plurality of discreet units are radially expandable, providing the elongate body an unexpanded configuration and a radially expanded configuration, and wherein the plurality of discreet units comprise a plurality of modular segments assembled around a longitudinal axis of the elongate cylindrical body to collectively define a central lumen, wherein each of the plurality of modular segments has a shape in the unexpanded configuration of the elongate body and retains the shape in the radially expanded configuration of the elongate body; and
delivering radiation therapy to the target tissue using the brachytherapy applicator.

46. The method of claim 45, wherein the plurality of discreet units comprise a plurality of segments having a similar configuration.

47. The method of claim 45, wherein the plurality of discreet units comprise a plurality of stackable components connected in a series.

48. The method of claim 45, further comprising expanding the elongate body from an unexpanded configuration to a radially expanded configuration.

49. The method of claim 45, further comprising removing the brachytherapy applicator from a vaginal canal.

50. The method of claim 45, wherein the radiation therapy is delivered by a radiation source.

51. The method of claim 50, wherein the radiation source comprises a radioactive liquid, an x-ray source, a radiation seed, or combinations thereof.

52. The method of claim 51, wherein the radiation source comprises radionuclides selected from the group consisting of cesium, iridium, iodine, cobalt, palladium, strontium, yttrium, gold, ruthenium, californium, and combinations thereof.

53. The method of claim 52, wherein the radiation source comprises iridium.

54. The method of claim 50, wherein the radiation source is loaded into the plurality of source lumens using an afterloader.

55. The method of claim 50, wherein the radiation source is used to treat a gynecological cancer.

56. The method of claim 55, wherein the gynecological cancer is selected from the group consisting of cervical cancer, endometrial cancer, uterine cancer, ovarian cancer, and vaginal cancer.

57. The method of claim 56, wherein the gynecological cancer is endometrial cancer.

58. The method of claim 57, wherein the radiation source delivers a total radiation dose of 10 Gy to 30 Gy to the target tissue to treat the endometrial cancer.

59. The method of claim 56, wherein the gynecological cancer is cervical cancer.

60. The method of claim 59, wherein the radiation source delivers a total radiation dose of 30 Gy to 45 Gy to the target tissue to treat the cervical cancer.

61. The method of claim 45, wherein the target tissue is the elongate portion of the uterus.

62. The method of claim 45, wherein the target tissue is the cervix.

63. The method of claim 45, wherein the target tissue is tissue of the vaginal wall or vaginal cuff.

* * * * *